US011524209B1

(12) United States Patent
Fung

(10) Patent No.: US 11,524,209 B1
(45) Date of Patent: Dec. 13, 2022

(54) BRAINWAVE ENTRAINMENT USING VIRTUAL OBJECTS AND GAMIFICATION

(71) Applicant: Blue Goji LLC, Austin, TX (US)

(72) Inventor: Coleman Fung, Austin, TX (US)

(73) Assignee: BLUE GOJI LLC, Austin, TX (US)

( * ) Notice: Subject to any disclaimer, the term of this patent is extended or adjusted under 35 U.S.C. 154(b) by 0 days.

(21) Appl. No.: 17/574,540

(22) Filed: Jan. 12, 2022

(51) Int. Cl.
| | |
|---|---|
| *A63F 13/212* | (2014.01) |
| *G06F 3/01* | (2006.01) |
| *A61B 5/375* | (2021.01) |
| *A61M 21/00* | (2006.01) |
| *A63B 24/00* | (2006.01) |
| *A63B 22/06* | (2006.01) |
| *A63B 22/02* | (2006.01) |
| *A63B 22/00* | (2006.01) |

(Continued)

(52) U.S. Cl.
CPC .......... *A63B 24/0003* (2013.01); *A61B 5/024* (2013.01); *A61B 5/375* (2021.01); *A63B 22/0046* (2013.01); *A63B 22/0285* (2013.01); *A63B 22/0292* (2015.10); *A63B 22/06* (2013.01); *A63B 23/04* (2013.01); *A63F 13/212* (2014.09); *A63F 13/214* (2014.09); *A63F 13/285* (2014.09); *A63F 13/40* (2014.09); *A63F 13/65* (2014.09); *A63F 13/80* (2014.09); *G06F 1/163* (2013.01); *G06F 3/011* (2013.01); *G06F 3/013* (2013.01); *G06F 3/015* (2013.01); *G06F 3/016* (2013.01); *G06T 19/006* (2013.01); *G16H 20/30* (2018.01); *A61M 2021/005* (2013.01); *A61M 2021/0022* (2013.01); *A61M 2021/0027* (2013.01); *A63F 2300/8082* (2013.01); *H04W 84/18* (2013.01)

(58) Field of Classification Search
CPC ............ A63B 24/0003; A63B 22/0046; A63B 22/0285; A63B 22/0292; A63B 22/06; A63B 23/04; A63F 13/212; A63F 13/214; A63F 13/40; A63F 13/65; A63F 2300/8082; A63F 13/245; A63F 13/285; A63F 13/428; A63F 13/80; G06F 1/163; G06F 3/011; G06F 3/016; G06F 2203/012; G06F 2203/013; G06F 3/0338; G06F 3/01; G06T 19/006; H04W 84/18; G16H 20/30; A61B 5/375; A61B 5/024
See application file for complete search history.

(56) References Cited

U.S. PATENT DOCUMENTS

| | | |
|---|---|---|
| 2019/0247662 A1 | 8/2019 | Poltroak |
| 2020/0356136 A1 | 11/2020 | Aimone et al. |
| 2021/0257080 A1* | 8/2021 | Iliffe-Moon ......... B60N 2/5621 |

* cited by examiner

*Primary Examiner* — Christine H Matthews
(74) *Attorney, Agent, or Firm* — Galvin Patent Law LLC; Brian R. Galvin

(57) ABSTRACT

A system and method for brainwave entrainment using virtual objects and gamification, in which brainwave entrainment is applied using some combination of gaming elements, and brainwave activity is enhanced by virtue of the user's active participation. Long-term use is encouraged by virtue of the entertaining nature of the gamification. Depending on configuration, the system and method may comprise a display comprising virtual objects, a light-producing device (other than the display), an audio-producing device such as speakers or headphones, a haptic feedback device such as a vibratory motor, and various devices for monitoring the user's attention. A software application induces brainwave entrainment via one or more of the devices of the system.

16 Claims, 15 Drawing Sheets

(51) Int. Cl.
*A63B 23/04* (2006.01)
*G06T 19/00* (2011.01)
*G06F 1/16* (2006.01)
*A63F 13/65* (2014.01)
*A63F 13/214* (2014.01)
*A63F 13/40* (2014.01)
*G16H 20/30* (2018.01)
*A61B 5/024* (2006.01)
*A63F 13/285* (2014.01)
*A63F 13/80* (2014.01)
*H04W 84/18* (2009.01)

BRAINWAVE ENTRAINMENT USING VIRTUAL OBJECTS AND GAMIFICATION

CROSS-REFERENCE TO RELATED APPLICATIONS

None.

BACKGROUND OF THE INVENTION

Field of the Art

This disclosure relates to the field of health and wellness therapies, and more particularly to systems and methods for rehabilitative and therapeutic neurological treatment using computer games and virtual environments.

Discussion of the State of the Art

Research increasingly highlights the importance of continued neurological stimulation throughout all stages of life including physical activity, social connection, and frequent cognitive challenge, especially when combined, in preventing early cognitive decline and onset of neurological disorders including dementia. As well, athletes and competitors in various fields such as physical, digital, and cognitive competitions are increasingly seeking well rounded methods of neurological evaluation and conditioning for tasks directly and indirectly related to their mode of competition.

Recent research on mice suggests that administration of light and sound at frequencies of gamma oscillations (30 Hz to 100 Hz) can help delay the onset of neurological decline or even cause neurological regeneration through gamma entrainment (see, Adaikkan et al., Gamma Entrainment Binds Higher-Order Brain Regions and Offers Neuroprotection, 2019, Neuron 102, 929-943, Jun. 5, 2019, and Martorell et al., Multi-sensory Gamma Stimulation Ameliorates Alzheimer's-Associated Pathology and Improves Cognition, 2019, Cell 177, 256-271, Apr. 4, 2019). These studies have suggested that light and/or sound-based gamma entrainment causes physical changes in the brain by stimulating oscillations in the electrochemical state of neurons in a way that reduces inflammation and increases synaptic density, and have suggested that gamma entrainment using simultaneous application of light and sound has a greater effect than gamma entrainment using only light or sound individually. The physical changes observed included reductions in amyloid plaques and tau phosphorylation, and decreases in neuronal and synaptic losses.

However, the studies performed to date are generalized in nature and do not provide specific systems or methods whereby this knowledge may be applied to humans. Further, these studies do not suggest any means for targeting the particular areas of the brain or particular neurological functionality affected by certain neurological disorders. These studies also fail to consider application of gamma entrainment through stimulation other than light or sound or application of multi-modal gamma entrainment other than simultaneous application of light and sound, or the use of other than physical stimulation transducers such as light emitting diodes (LEDs). Additionally, these studies do not explore the effects of treatment regimens of entrainment to frequencies inducing brain activity other than gamma waves or utilizing a combination of frequencies at various intervals.

Further, as currently known, brainwave entrainment consists of solely of boring, repetitive listening to certain audio frequencies or staring at flashing physical lights. Thus, brainwave entrainment is a purely passive, boring activity, which quickly leads to abandonment of the activity and little or no benefit.

What is needed is a system and method which applies brainwave entrainment using virtual objects and/or gamification.

SUMMARY OF THE INVENTION

Accordingly, the inventor has conceived and reduced to practice, a system and method for brainwave entrainment using gamification, in which brainwave entrainment is applied using some combination of gaming elements, brainwave activity is enhanced by virtue of the user's active participation, and long-term use is encouraged by virtue of the entertaining nature of the gamification. Depending on configuration, the system and method may comprise a display comprising virtual objects, a light-producing device (other than the display), an audio-producing device such as speakers or headphones, a haptic feedback device such as a vibratory motor, a means for monitoring the user's attention, and a software application which applies brainwave entrainment using some combination of the display, the light-producing device, the audio-producing device, and the haptic feedback device. In some embodiments, the brainwave entrainment may be based in part on the monitoring of the user's attention. In some embodiments, virtual objects on the display may be used to provide brainwave entrainment. Some embodiments may comprise additional components such as an entrainment routine selector which adjusts the brainwave entrainment based on certain inputs, biometric sensors such as an electroencephalograph which may be used to provide inputs to the software application or entrainment routine selector. In some embodiments, brainwave entrainment may be applied using combinations of brainwave entrainment from virtual objects on the display and physical stimulation transducers such as the light-producing device, the audio-producing device, and the haptic feedback device. In some embodiments, the software application is a virtual reality environment, and the display may be a virtual reality headset or other virtual reality display hardware.

According to a preferred embodiment, a system for brainwave entrainment using gamification is disclosed, comprising: a computing device comprising a memory and a processor; a stimulation transducer; a brainwave entrainment manager comprising a first plurality of programming instructions stored in the memory and operating on the processor, wherein the first plurality of programming instructions, when operating on the processor, causes the computing device to: receive a therapy regimen for brainwave entrainment; select an entrainment frequency based on the therapy regimen; receive game play data from a game application, the game play data comprising an interaction with the game; based on the therapy regimen selected, instruct the game application to change a state of the stimulation transducer at the selected entrainment frequency or range of entrainment frequencies; and the game application comprising a second plurality of programming instructions stored in the memory and operating on the processor, wherein the first plurality of programming instructions, when operating on the processor, causes the computing device to: operate a game on the computing device, the game comprising one or more opportunities for interaction; receive the instruction to change the state of the stimulation transducer; and change the state of the stimulation transducer at the selected entrainment frequency or range of entrainment frequencies.

According to another preferred embodiment, a method for brainwave entrainment using gamification is disclosed, comprising the steps of: receiving, at a brainwave entrainment manager operating on a computing device, a therapy regimen for brainwave entrainment; selecting an entrainment frequency or range of entrainment frequencies based on the therapy regimen; operating a game on the computing device using a game application operating on the computing device, the game comprising one or more opportunities for interaction; receiving game play data from the game application, the game play data comprising an interaction with the game; based on the therapy regimen selected, instructing the game application to change a state of a stimulation transducer at the selected entrainment frequency or range of entrainment frequencies; and changing, using the game application, the state of the stimulation transducer at the selected entrainment frequency.

According to an aspect of an embodiment, the brainwave entrainment manager is further configured to change one or more of the entrainment frequencies based on feedback.

According to an aspect of an embodiment, the feedback comprises determination of a user's attention based on the user's interaction with the virtual object.

According to an aspect of an embodiment, a biometric sensor is used to measure biometric data from the user, and wherein the feedback comprises the biometric data.

According to an aspect of an embodiment, the biometric sensor is a heart rate monitor and the biometric data is a heart rate of the person.

According to an aspect of an embodiment, the biometric sensor is an electroencephalograph (EEG) and the biometric data is an electrical activity of the brain of the person.

According to an aspect of an embodiment, a spatial sensor is used to measure a location in physical space, and wherein the feedback comprises the spatial sensor data.

According to an aspect of an embodiment, the spatial sensor is an eye-tracking sensor.

According to an aspect of an embodiment, a display is provided and stimulation transducer is a virtual object on the display.

According to an aspect of an embodiment, the stimulation transducer is selected from the list of a visual stimulation transducer, an auditory stimulation transducer, a vibratory stimulation transducer, a haptic headband comprising vibratory feedback, and a game controller comprising vibratory feedback.

BRIEF DESCRIPTION OF THE DRAWING FIGURES

The accompanying drawings illustrate several embodiments of the invention and, together with the description, serve to explain the principles of the invention according to the embodiments. It will be appreciated by one skilled in the art that the particular embodiments illustrated in the drawings are merely exemplary, and are not to be considered as limiting of the scope of the invention or the claims herein in any way.

Figure 8:
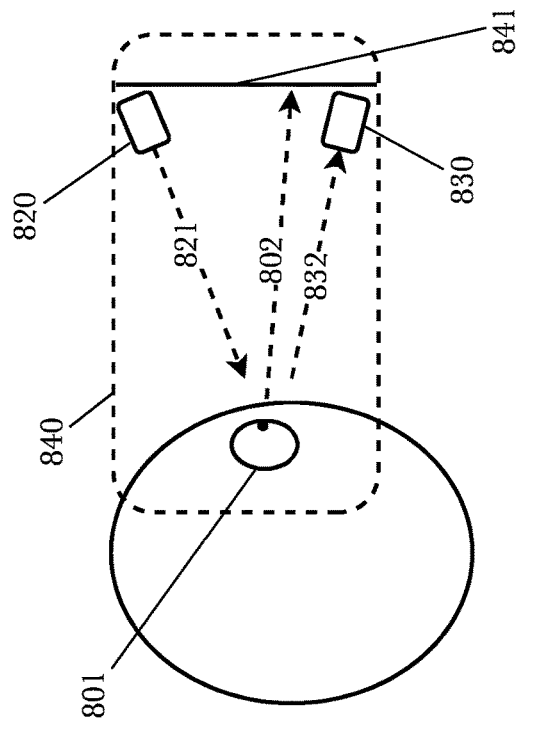
Figure 7:
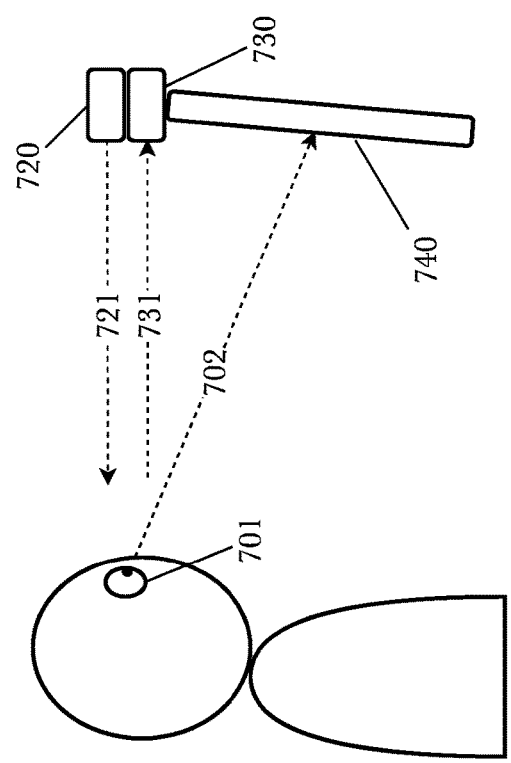
Figure 9:
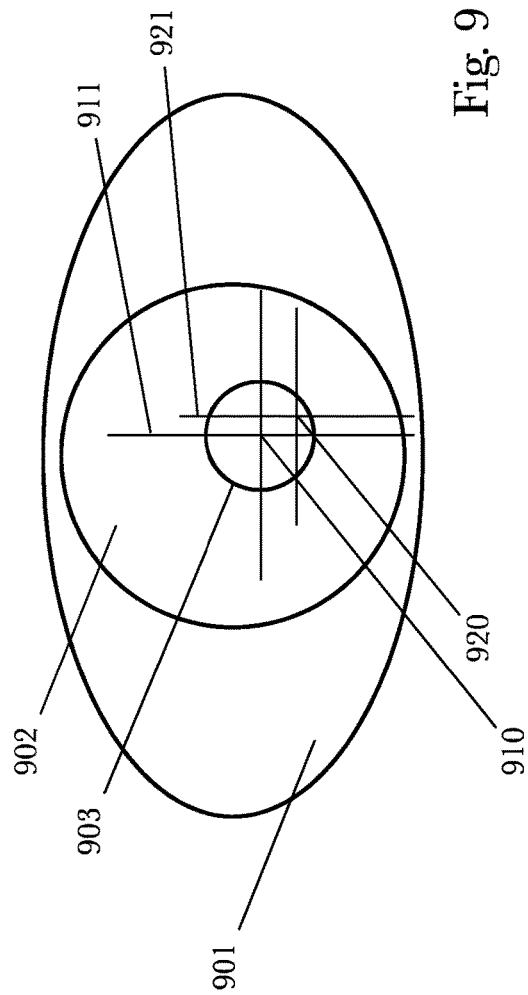

FIGS. 7-9 explain the application of eye tracking technology as a means of determining where a user is looking.

Figure 10:
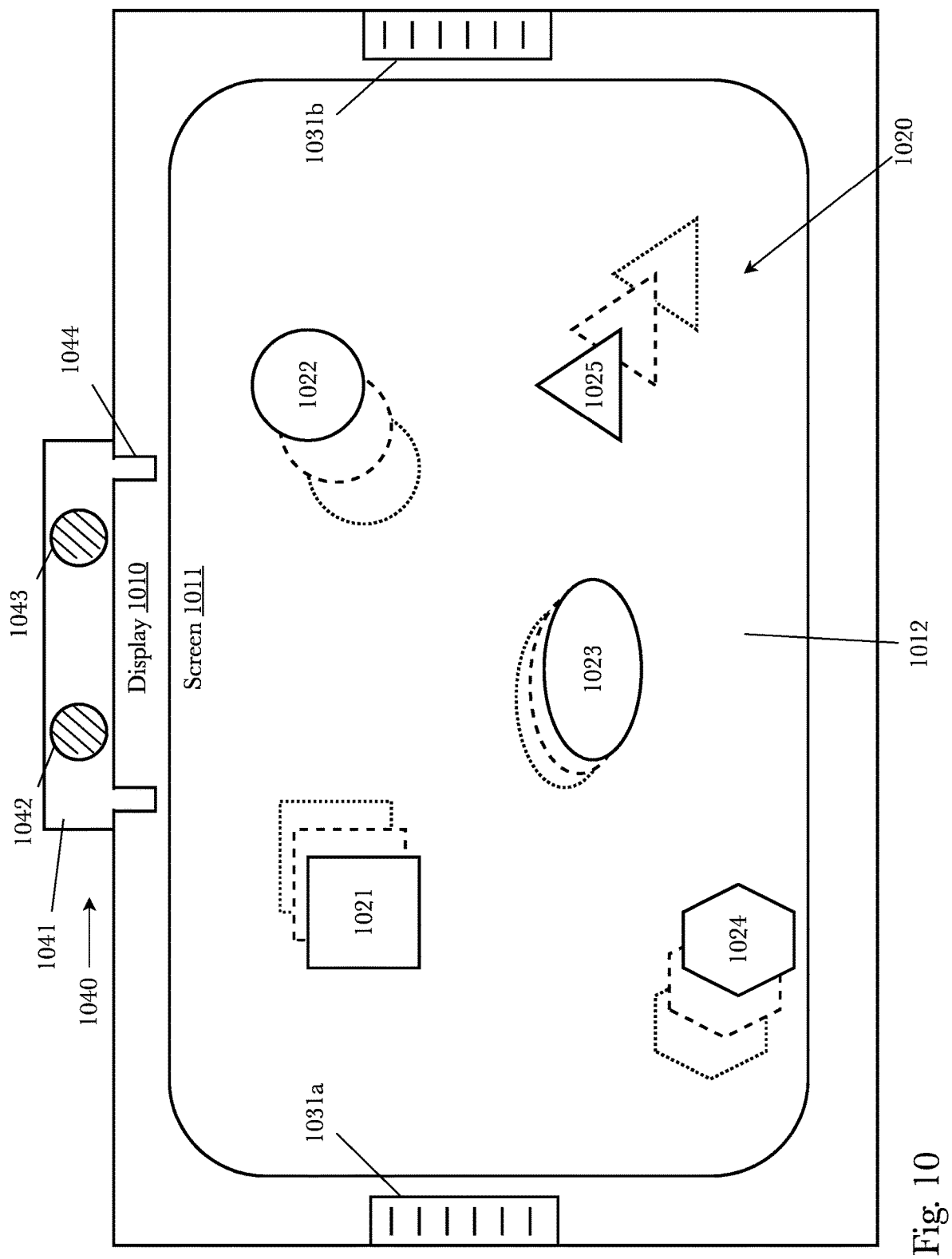

FIG. 10 is a diagram showing an embodiment in which on-screen elements of a display are used to apply brainwave entrainment in conjunction with eye tracking.

Figure 11:
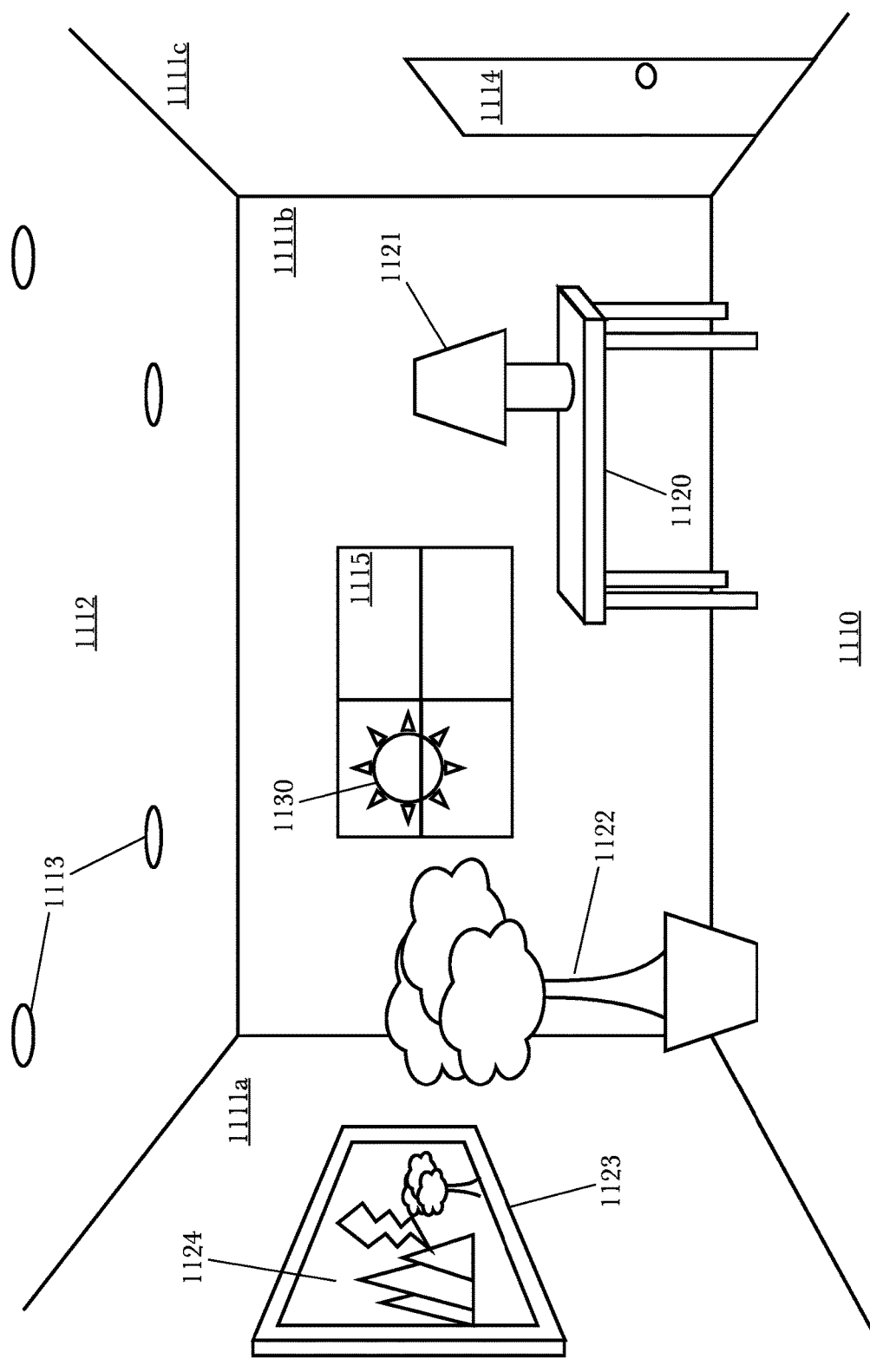

FIG. 11 is a diagram showing an exemplary virtual reality environment in which virtual objects may be used as visual stimulation transducers.

Figure 12:
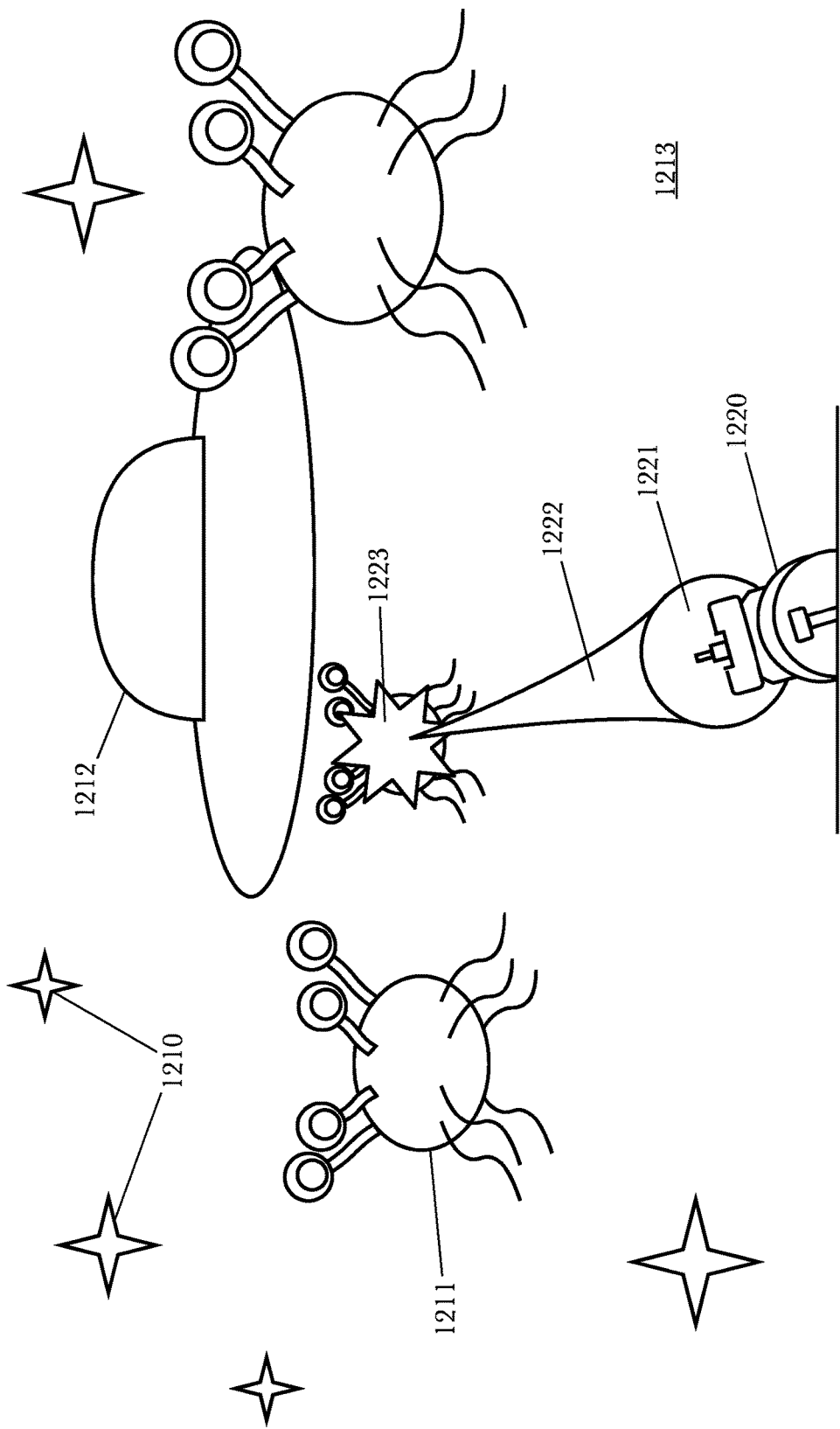

FIG. 12 is a diagram showing exemplary gamification of brainwave entrainment in which in-game objects and elements are used as visual stimulation transducers in conjunction with gameplay activities.

Figure 13:
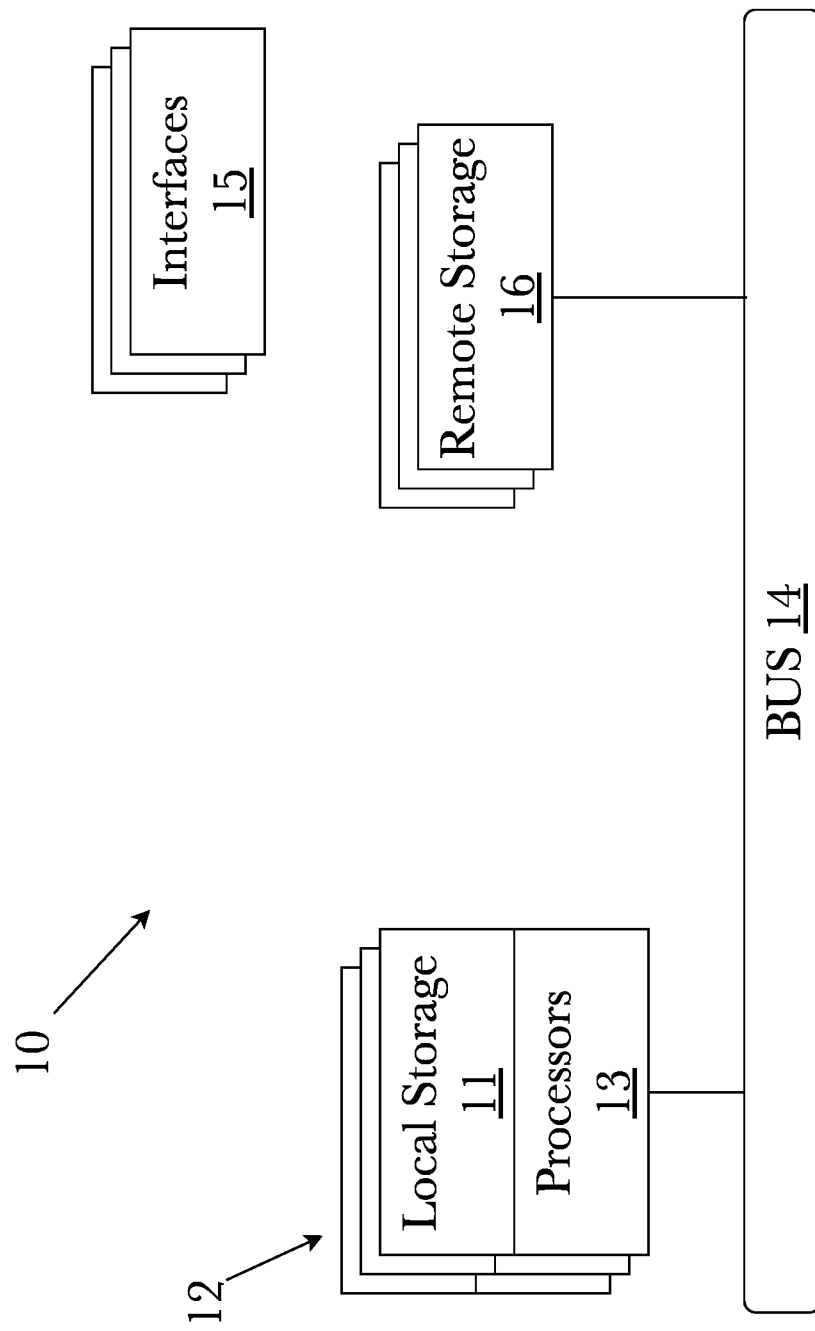

FIG. 13 is a block diagram illustrating an exemplary hardware architecture of a computing device.

Figure 14:
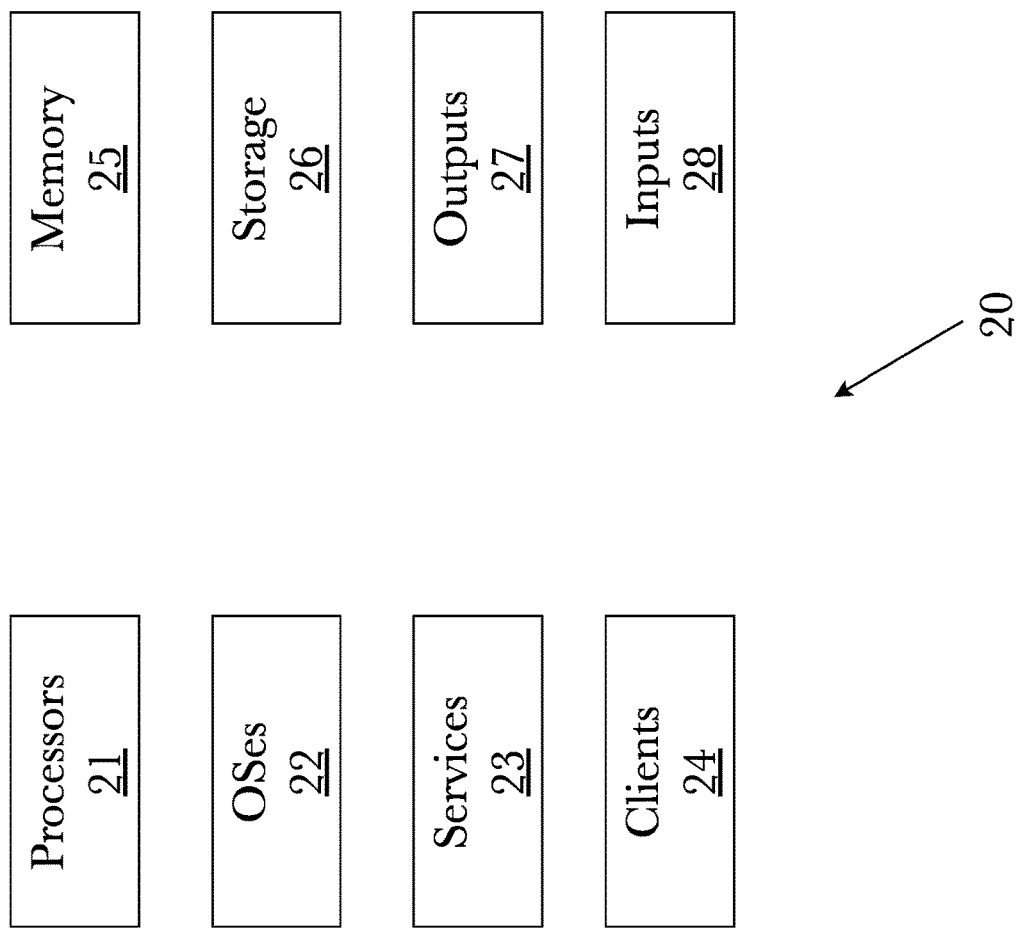

FIG. 14 is a block diagram illustrating an exemplary logical architecture for a client device.

Figure 15:
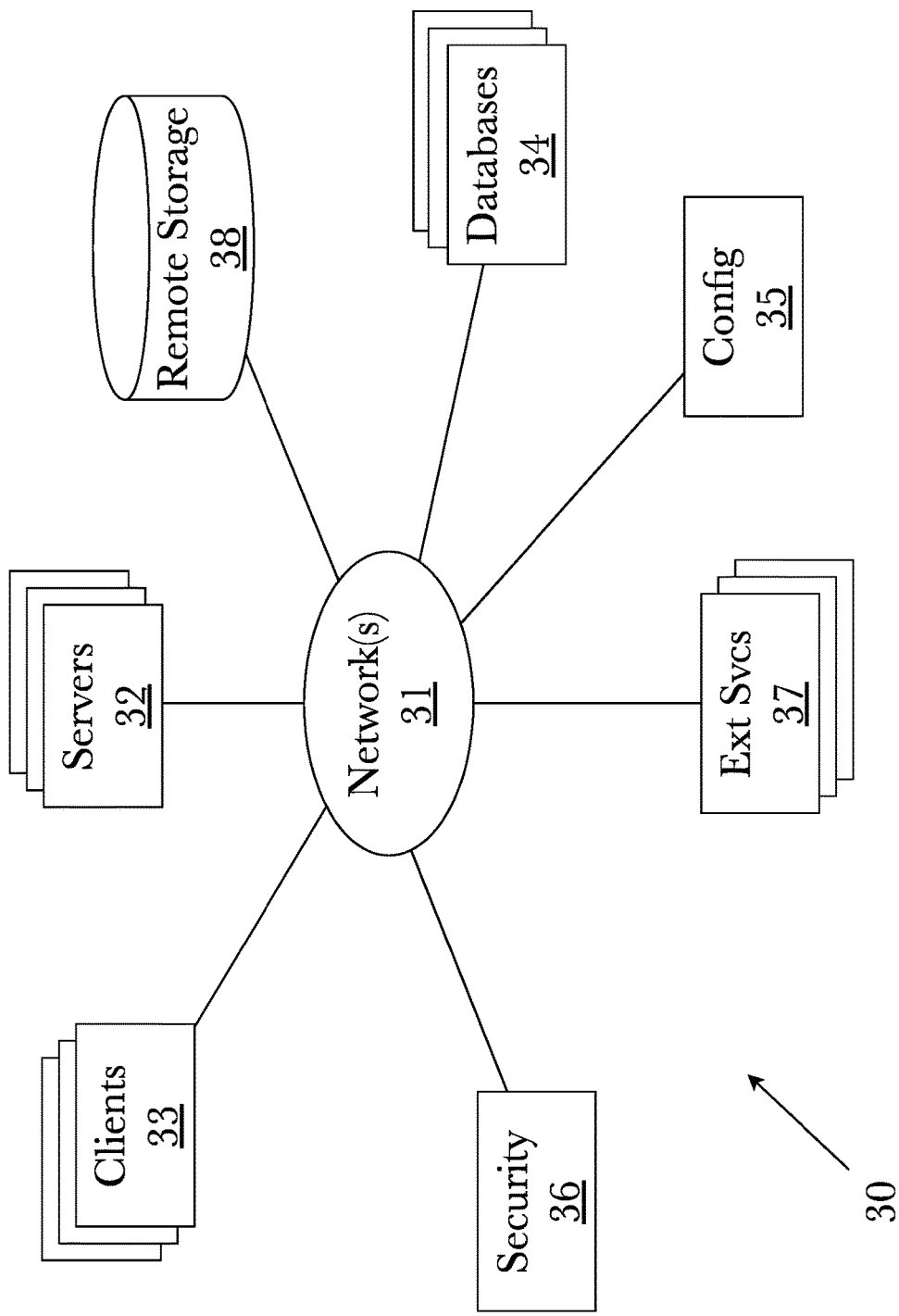

FIG. 15 is a block diagram showing an exemplary architectural arrangement of clients, servers, and external services.

Figure 16:
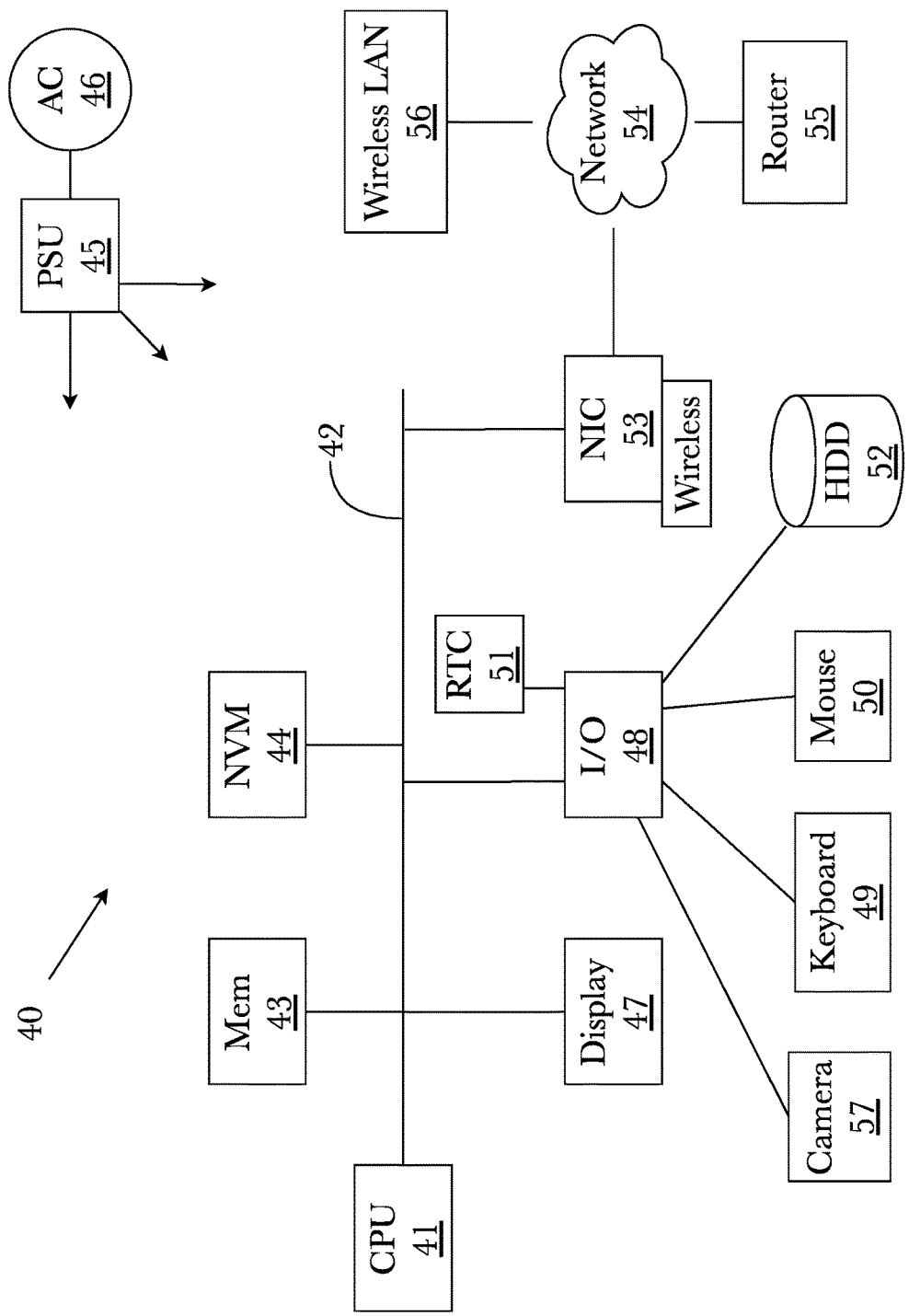

FIG. 16 is another block diagram illustrating an exemplary hardware architecture of a computing device.

DETAILED DESCRIPTION

The inventor has conceived, and reduced to practice, a system and method for brainwave entrainment using gamification, in which brainwave entrainment is applied using some combination of gaming elements, brainwave is enhanced by virtue of the user's active participation, and long-term use is encouraged by virtue of the entertaining nature of the gamification. Depending on configuration, the system and method may comprise a display comprising virtual objects, a light-producing device (other than the display), an audio-producing device such as speakers or headphones, a haptic feedback device such as a vibratory motor, a means for monitoring the user's attention, and a software application which applies brainwave entrainment using some combination of the display, the light-producing device, the audio-producing device, and the haptic feedback device. In some embodiments, the brainwave entrainment may be based in part on the monitoring of the user's attention. In some embodiments, virtual objects on the display may be used to provide brainwave entrainment. Some embodiments may comprise additional components such as an entrainment routine selector which adjusts the brainwave entrainment based on certain inputs, biometric sensors such as an electroencephalograph which may be used to provide inputs to the software application or entrainment routine selector. In some embodiments, brainwave entrainment may be applied using combinations of brainwave entrainment from virtual objects on the display and physical stimulation transducers such as the light-producing device, the audio-producing device, and the haptic feedback device. In some embodiments, the software application is a virtual reality environment, and the display may be a virtual reality headset or other virtual reality display hardware.

Implementations of visual brainwave entrainment to date have been limited to passive visual stimulation using physical lights (typically light emitting diodes, or LEDs). There is no interactivity or active engagement with the visual stimulation transducers, which makes the process less effective and uninteresting. Further, the visual stimulation transducers, being physical objects, cannot be changed in terms of size or shape, cannot be modified in reaction to user feedback, and are limited in terms of colors available, are generally fixed in place, and additional lights cannot be added to the system without physically connecting (and likely programming) additional lights.

Virtual objects, on the other hand, have none of these limitations, and can be used as visual stimulation transducers while users are engaged with an on-screen display. Brainwave entrainment using virtual objects provides essentially unlimited variability in terms of stimulator sizes, shapes, colors, movements, rotations, etc., and allows for the use of multiple stimulators simultaneously, each with different characteristics. Any change to a virtual object that is perceptible to a user and can be applied at a repeating frequency may be used to apply brainwave entrainment.

Further, gamification changes the brainwave stimulation from passive receipt of light therapy to active engagement with the visual stimulation objects, wherein the user's brain is actively stimulated during the activity, enhancing the effectiveness of the stimulation. Further, as the user is actively engaged with the game, stimulation can be applied based on where the user's attention is focused. Attention-based stimulation provides opportunities for both direct stimulation (e.g., flashing an object at which the user is looking, playing sounds or providing haptic feedback associated with a game object or activity that is the object of the user's attention, etc.) and indirect stimulation (e.g., flashing an object in the user's periphery of vision, playing sounds or providing haptic feedback associated with the game, but not the object of the user's attention such as a background element, background music or sounds, etc.). For example, eye tracking technology can be used to determine where the user is looking on the screen at any given time, and objects at which the user is looking can be used to provide visual stimulation even if the user changes his or her attention to a different object on the screen. The user's attention to objects on the screen can be monitored over time to determine whether the user is remaining focused on the activity, or is getting tired and losing focus, and the determined level of user attention can be used to change the type, intensity, directness, and other characteristics of the stimulation. Other means of determining the user's attention may be used such as assuming that the user's attention is focused on an object with which the user has just interacted.

Brainwave entrainment using virtual objects may be further enhanced by using multiple objects, each capable of providing complementary types of stimulation, and/or by intentionally directing the user's attention to objects providing certain types of stimulation. For example, if the user is playing a first person shooter (FPS) game that involves shooting attacking aliens, the user's attention will naturally be focused on finding attacking aliens, aiming at them, and shooting them. As each alien will be the focus of the user's attention sequentially, the alien at which the user is currently looking may be flashed at appropriate frequencies and in appropriate colors to provide appropriate brainwave stimulation. Simultaneously, other objects on the screen (or even the background) may be selected to provide a complementary visual stimulation in the periphery of the user's vision. Further, brainwave entrainment using virtual objects may be enhanced by selecting multiple treatment modalities (e.g., light, sound, vibration, electrical stimulation) applied either simultaneously or sequentially, by varying the frequency or frequencies of brainwave entrainment (e.g., from about 0.5 Hz to about 100 Hz), and by varying the intensity and/or scale of the treatment (e.g., from subtle, localized vibrational or electrical stimulation to area-wide, intense stimulation such as high-intensity room lighting and sound).

Brainwaves are frequencies at which electrical impulses in the brain occur. Brainwave frequencies change based on the state of consciousness of the user (e.g., sleeping, awake, dreaming, concentrating, relaxed, contemplative, meditative, irritated, etc.). Generally speaking, brainwaves are divided into five categories with frequencies roughly in the following ranges.

Delta waves are brainwaves in the general frequency range of 0.1 Hz to 4 Hz. Delta waves occur during deep sleep, and indicate a low level of arousal. Theta waves are brainwaves in the general frequency range of 4 Hz to 8 Hz. Theta waves occur in a state between wakefulness and sleep, such as during daydreaming and meditation, and can indicate drowsiness, creativity, or imagination. Alpha waves are brainwaves in the general frequency range of 8 Hz to 12 Hz. Alpha waves occur during a waking state, but are associated with relaxation, problem solving, analysis, and decision-making. Beta waves are brainwaves in the general frequency range of 12 Hz to 30 Hz. Beta waves occur during alertness, concentration, and strenuous mental activities such as solving mathematical problems and planning for the future. Gamma waves are brainwaves in the general frequency range of 30 Hz to 44 Hz. Gamma waves are associated with high-level information processing. There is evidence of Lambda brainwaves in a range around 47 Hz to 70 Hz, and other brainwave entrainment frequencies may be useful up to around 100 Hz. These ranges are approximate, and there is some overlap between them.

There are many promising uses of brainwave entrainment. One promising use of brainwave entrainment is to treat and/or prevent epilepsy. There is some evidence that epileptic seizures occur when the brain falls into theta wave activity (approximately 4 Hz to 8 Hz) during normal waking consciousness. Normal waking consciousness is typically associated with beta wave brain activity (12 Hz to 38 Hz). Performing brainwave entrainment at beta wave frequencies on persons with epilepsy may help prevent them from falling into theta wave brain activity, thus preventing seizures.

Another possible use for brainwave entrainment is to reduce agitation by performing brainwave entrainment at alpha wave frequencies (approximately 8 Hz to 12 Hz). Alpha wave frequencies are those brain wave frequencies between theta wave activity (typically associated with dreaming) and beat wave activity (typically associated with concentration and learning). Alpha wave frequencies are associated with relaxation and calmness. Therefore, brainwave entrainment at alpha wave frequencies may help induce relaxation and calmness.

Many different wave forms and/or pulse widths may be used in delivering entrainment at the selected frequency or frequencies, regardless of the modality (light, sound, etc.) of the stimulation. Wave forms may include, but are not limited to, rectangular wave forms, sine wave forms, triangular wave forms, and sawtooth wave forms. Pulse widths or duty cycles at any given frequency may be varied across the entire range of the frequency period. For example, at a given frequency, the duty cycle of each period of the frequency can be varied from nearly 0% on-time/100% off-time to nearly 100% on-time/0% off-time. Thus, for a given frequency, the stimulator (e.g., light) can be on and off for an equal amount of time in each period (a 50% duty cycle), mostly on during each period (e.g., a 75% duty cycle), or mostly off during each period (e.g., a 25% duty cycle). In these cases, the frequency of the stimulation is the same, but the amount of on-time of the stimulation in each period of the frequency is different.

Different pulse widths or duty cycles may be useful, depending on the circumstances. For example, when engaged in a mental task that requires visual acuity, a very low or very high duty cycle may be used to flash a light stimulator at a pulse width that can be captured by the human eye, but is not consciously recognizable. The human eye can capture flashes of light as short as $1/200^{th}$ of a second (equivalent to a frequency of 200 Hz), possibly shorter, but because of persistence of vision, cannot distinguish between repeated flashes of light at that frequency. Television and computer monitor frame refresh rates are typically 60 Hz or above, as this is a frequency at which persistence of vision makes it difficult to distinguish between frames. Thus, for example, the flicker of light stimulation at a frequency of 40 Hz and a 50% duty cycle would be easily perceivable by most human beings as each "on" pulse is $1/80^{th}$ of a second long and separated by another "off" time of another $1/80^{th}$ of a second. However, the flicker of light stimulation at the same frequency, but at a 80% duty cycle would likely not be consciously perceptible, as the "on" time of each period would last about $1/50^{th}$ of a second and the "off" time of each period would last about $1/200^{th}$ of a second. Thus, the "off" time of each period is within the limits of capture by the human eye (200 Hz), but would likely not be consciously perceptible because it is above the average frequency resolution (60 Hz) of the human eye, and the light would appear to the conscious mind to be on all the time.

In a similar manner, pulse widths or duty cycles may be adjusted to be perceptible to certain cells in the eye but not others. The human eye has two different types of light receptors: cones and rods. Cones are the dominant light receptors used under daylight conditions, and reception of light by cones is called photopic vision. Cones are able to distinguish colors, but are less sensitive to lower light intensity and the persistence of vision of cones is greater (meaning that the frequency of pulses that can be distinguished by cones is less than for rods). Rods are the dominant light receptors used at night and under low-light conditions, and reception of light by rods is called scotopic vision. Rods are not able to distinguish colors, but are more sensitive to lower light intensity and the persistence of vision of rods is less (meaning that the frequency of pulses that can be distinguished by rods is greater than for cones). Cones are greatly concentrated in the center of vision (where the person is directly looking) while rods are considerably more dominant in the periphery of vision. This difference in the type of light receptors in the eye can be used to advantage when selecting either a frequency of stimulation or a pulse width/duty cycle of that frequency. Again using the example above where visual acuity is required for a mental task, the pulse width or duty cycle of each period of a brainwave entrainment frequency of light can be selected to be perceptible to rods but not to cones, thus allowing the brainwave entrainment frequency of light to be perceived by the brain (through the rods in the periphery of vision which have a greater frequency resolution), but not consciously perceptible to the person (who is primarily focused on the light received by the cones (in the center of vision and with a lesser frequency resolution). One or more different inventions may be described in the present application. Further, for one or more of the inventions described herein, numerous alternative embodiments may be described; it should be appreciated that these are presented for illustrative purposes only and are not limiting of the inventions contained herein or the claims presented herein in any way. One or more of the inventions may be widely applicable to numerous embodiments, as may be readily apparent from the disclosure. In general, embodiments are described in sufficient detail to enable those skilled in the art to practice one or more of the inventions, and it should be appreciated that other embodiments may be utilized and that structural, logical, software, electrical and other changes may be made without departing from the scope of the particular inventions. Accordingly, one skilled in the art will recognize that one or more of the inventions may be practiced with various modifications and alterations. Particular features of one or more of the inventions described herein may be described with reference to one or more particular embodiments or figures that form a part of the present disclosure, and in which are shown, by way of illustration, specific embodiments of one or more of the inventions. It should be appreciated, however, that such features are not limited to usage in the one or more particular embodiments or figures with reference to which they are described. The present disclosure is neither a literal description of all embodiments of one or more of the inventions nor a listing of features of one or more of the inventions that must be present in all embodiments.

Headings of sections provided in this patent application and the title of this patent application are for convenience only, and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an embodiment with several components in communication with each other does not imply that all such components are required. To the contrary, a variety of optional components may be described to illustrate a wide variety of possible embodiments of one or more of the inventions and in order to more fully illustrate one or more aspects of the inventions. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the invention(s), and does not imply that the illustrated process is preferred. Also, steps are generally described once per embodiment, but this does not mean they must occur once, or that they may only occur once each time a process, method, or algorithm is carried out or executed. Some steps may be omitted in some embodiments or some occurrences, or some steps may be executed more than once in a given embodiment or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other embodiments of one or more of the inventions need not include the device itself.

Techniques and mechanisms described or referenced herein will sometimes be described in singular form for clarity. However, it should be appreciated that particular embodiments may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of embodiments of the present invention in which, for example, functions may be executed out of order from that shown or discussed, including substantially concurrently or in reverse order, depending on the functionality involved, as would be understood by those having ordinary skill in the art.

Definitions

The term "amplitude" means the difference between the high or low state of a signal or wave form and the base state of that signal or wave form in a full period (high/low or on/off cycle) of the frequency of the signal or wave form.

The term "biometrics" as used herein mean data that can be input, directly measured, or computed using directly measured data from a user. This data includes but is not limited to physical and virtual movement, physiological, biological, behavioral, navigational, cognitive, alertness and attention, emotional, and brainwave measurements and patterns.

The phrase "brainwave entrainment" means application of a stimulus with a frequency from about 0.5 Hz to about 100 Hz as a means of neurological therapy. The stimulus may be of any perceptible form such as, but not limited to, light, sound, vibration, or electrical stimulation. The stimulus need not be from the same source (e.g., two light sources each at 20 Hz could be synchronized to produce a 40 Hz stimulus) or from the same modality (e.g., a sound source at 15 Hz and a light source at 15 Hz could be synchronized to produce a 30 Hz stimulus).

The term "conditioning" as used herein means all aspects of the system that can be used for the improvement, training, treatment of or exposure to aspects of neurological functioning. This could be in the form of a prescribed regimen from an expert, recommendation algorithm, self-selected experiences, or combination thereof.

The term "display" means any type of device capable of producing an output visible to a user of the system. A non-limiting list of displays includes televisions, computer monitors, tablet and mobile phone screens, VR headsets, and projectors.

The phrase "duty cycle" means the amount of time that a frequency signal is in the "high" or "on" state, expressed as a percentage, wherein each full period (complete high/low cycle) of the frequency signal represents 100%. Note that "duty cycle" and "pulse width" are two different means of expressing the same concept.

The term "expert" as used herein means an individual with specialization in an area via formal training, credentials, or advanced proficiency in a modality of interest to the user or with regard to neurological functioning. This includes but is not limited to physicians, psychiatrists, physical therapists, coaches, fitness trainers, high level athletes or competitors, and teachers.

The term "frequency" means a signal or wave form having a periodic repetition of high/low or on/off states. Examples of signals and wave forms that exhibit the characteristic of frequency include, but are not limited to, rectangular wave forms, sine wave forms, triangular wave forms, and sawtooth wave forms.

The terms "game" or "game application" mean any computer game, puzzle, display, animation, or simulation comprising virtual objects that can be interacted with in some manner by a person. These phrases include, but are not limited to, traditional two-dimensional games and puzzles, three-dimensional virtual reality (VR) applications and environments, enhanced reality and augmented reality applications and environments (comprising both real-world elements and virtual elements, such as virtual objects superimposed on a video feed of the real environment surrounding the user), and interactive applications that allow one to sense virtual objects through haptic feedback (whether or not associated with a visual display of the objects).

The term "gamification" as used herein means the application of brainwave entrainment using a game or a game application.

The phrases "neurological functioning" and "neurological function" as used herein mean any and all aspects of neuroscience and neurology where input, output, processing, or combination thereof involve aspects of the nervous system. These include but are not limited to functional as well as anatomical aspects of cognitive, sensory, motor, emotional, and behavioral functions and experiences.

The phrase "pulse width" means the amount of time that a frequency signal is in the "high" or "on" state, expressed as a time period that is a portion of each full period (complete high/low cycle) of the frequency signal. Note that "duty cycle" and "pulse width" are two different means of expressing the same concept. The phrase "pulse width modulation" is often used to denote changing of the pulse width of a frequency signal.

The term "transducer" as used herein means a device that converts an electrical signal into variations in a physical quantity, such as sound, light, pressure, or electrical stimulation. A display is included in the definition of "transducer."

The phrase "stimulation transducer" as used herein means a transducer used to stimulate one of the senses of a person or animal. Any portion of a display may be used as a stimulation transducer, non-limiting examples of which include virtual objects or backgrounds on the display.

The phrase "virtual object" means a computer-generated simulation of an object perceivable to a human being.

Virtual objects include, but are not limited to, visible virtual objects such as two-dimensional and three-dimensional shapes shown on a display, non-visible virtual objects such as those that might be "felt" through haptic feedback (e.g., gloves equipped with haptic feedback equipment that provide resistance to the user's fingers around the contours of a virtual object in space), and any combination of the two (e.g., a visible virtual object displayed in a virtual reality environment through a VR headset which can also be "felt" by the user via haptic feedback). A virtual object does not have to be gamified and may be, for example, a virtual object displayed on a screen.

Conceptual Architecture

Figure 1:
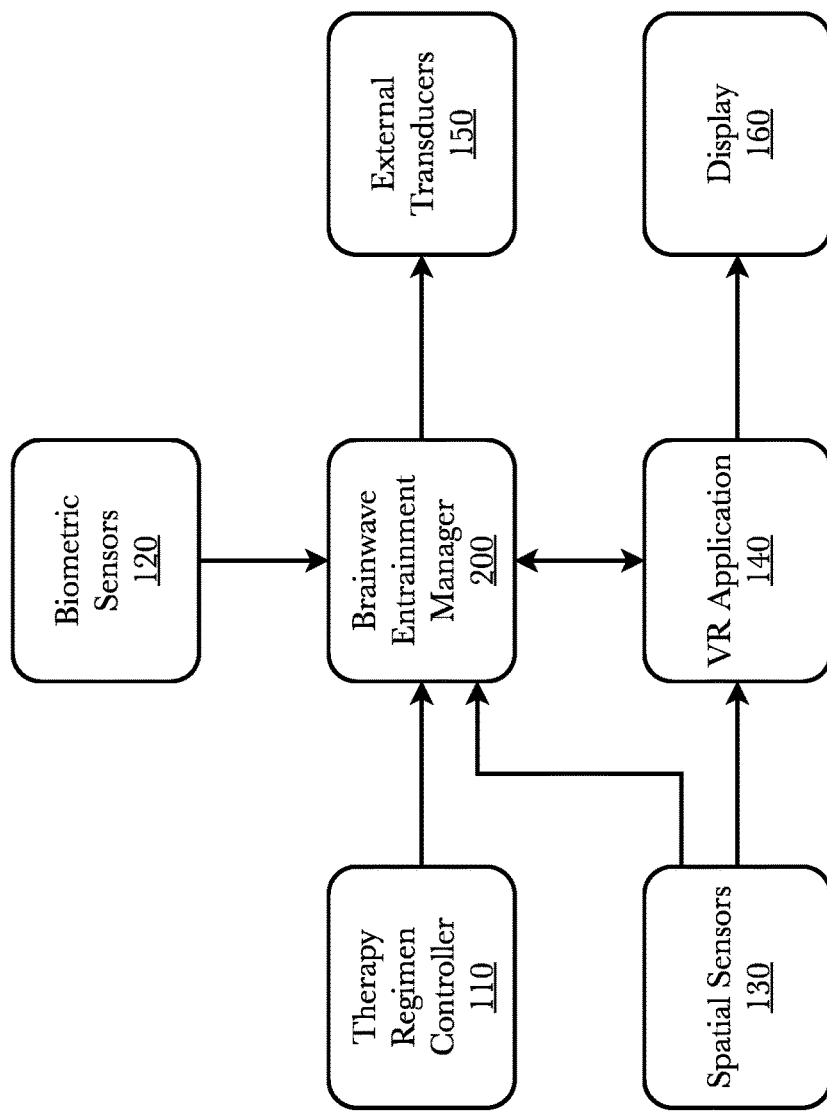
FIG. 1 is a diagram showing an exemplary overall system architecture for a brainwave entrainment system using virtual objects and environments as visual, stimulation transducers.

FIG. 1 is a diagram showing an exemplary overall system architecture 100 for a brainwave entrainment system using virtual objects and environments as visual stimulation transducers. In this embodiment, the system comprises a brainwave entrainment manager 200, a virtual reality (VR) application 140, a therapy regimen controller 110, one or more spatial sensors 130, one or more biometric sensors 120, and one or more external transducers, and a display 160.

The brainwave entrainment manager 200 is the core of the system, and manages inputs from, and outputs to, other components of the system. It is responsible for selection of entrainment routines, evaluation of the user's attention, and activation of both virtual and physical stimulation transducers.

The therapy regimen controller 110 is an administrative interface that allows an administrator (e.g., a physician, therapist, masseuse, or other service provider) to select therapy regimens for application to the user (who may be a patient, client, etc., of the administrator). The therapy regimen controller 110 may be used, for example, to select a regimen for brainwave entrainment that emphasizes alpha wave stimulation to induce relaxation in an overstimulated user.

The biometric sensors 120 are sensors that measure a physical or physiological characteristic of the user, such as heart rate, temperature, sweat production, brain activity (using an electroencephalograph, or EEG), etc. Biometric sensors 120 are used to provide feedback to the brainwave entrainment manager 200 as to the physical or physiological state of the user, which may be used to infer the user's mental state. For example, a biometric sensor 120 that measures the user's heart rate may be used to infer the user's level of relaxation (or lack thereof), thus providing feedback as to the effectiveness of alpha brainwave entrainment intended to induce relaxation.

Spatial sensors 130 are sensors that measure a user's physical location in space or a location at which the user is focusing his or her attention. For two dimensional screens, eye movement may be tracked and the location of the user's gaze may be calculated. In the case of virtual reality (VR), the user's body may be tracked, or if the user is wearing a VR headset, the orientation of the headset can be used to detect the user's head movements. Spatial sensors 130 are used to detect the user's engagement with virtual objects and virtual environments, such that brainwave entrainment using those objects and environments can be adjusted, accordingly.

The VR application 140 is used for gamification of brainwave entrainment. While a VR application 140 is shown here, in principle any computer game, puzzle, display, or animation can be used, whether interactive or not, and whether three-dimensional or two-dimensional. The VR application 140 can be a specially-designed program intended for use with the system, or can be an off-the-shelf game or application adapted for use with the system. In either case, the VR application 140 will either have an interface with the brainwave entrainment manager 200, or will have a brainwave entrainment manager 200 integrated into it, whereby the brainwave entrainment manager 200 is used to control brainwave entrainment using the virtual objects in the VR application 140.

The external transducers 150 are physical stimulation transducers that may be used to complement brainwave entrainment using virtual objects. A non-limiting list of external transducers 150 includes lights or LEDs, speakers or other audio-producing devices, vibratory or other pressure-producing devices, and electrical stimulators. As an example, while brainwave entrainment is being applied visually using virtual objects on a screen, the brainwave entrainment may be supplemented or complemented by audible brainwave entrainment using speakers.

The display 160 may be any type of display producing an output visible to a user of the system. A non-limiting list of displays 160 includes computer and tablet screens, VR headsets, and projectors. The display 160 is the means by which visual brainwave entrainment may be applied using virtual objects.

Figure 2:
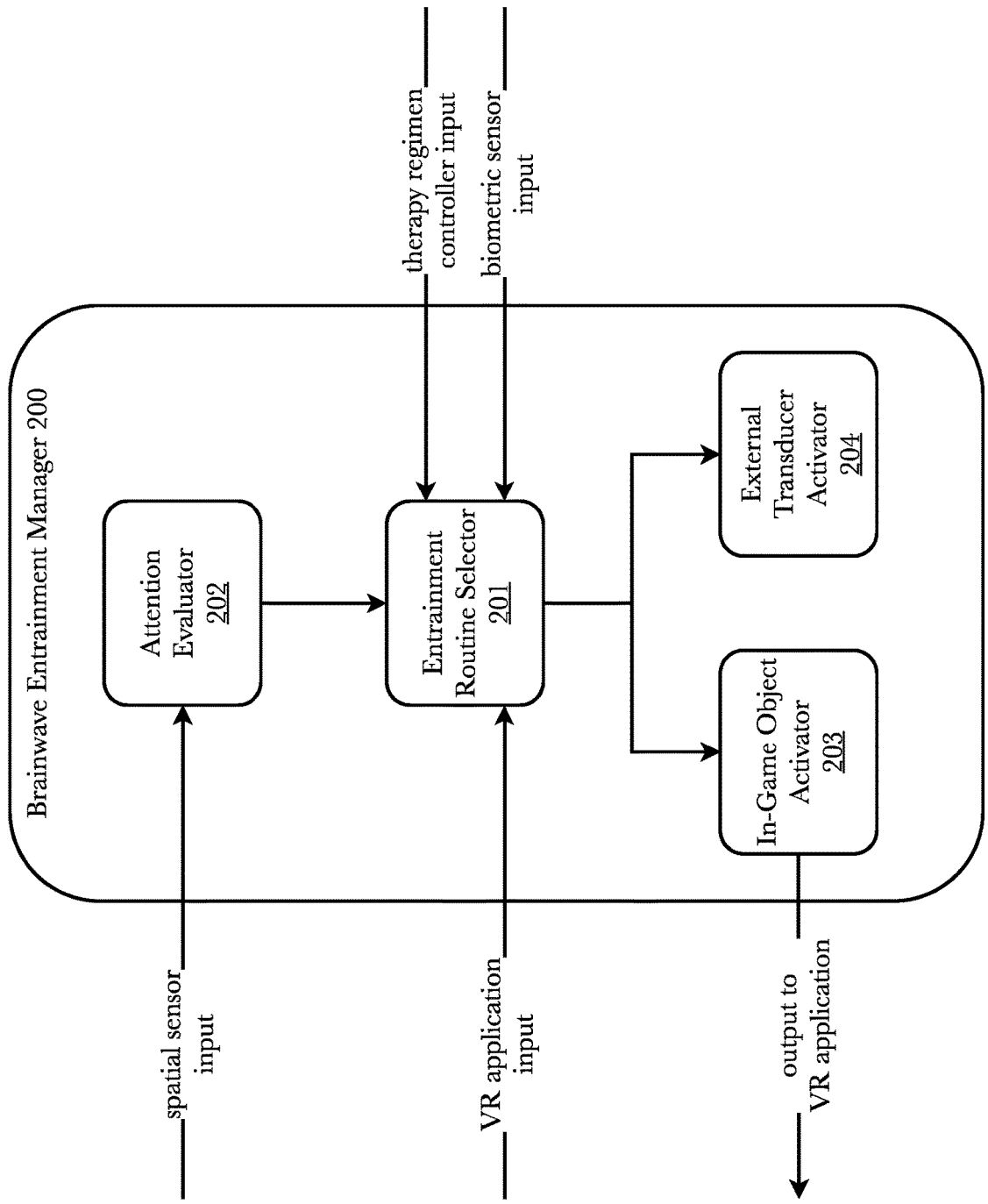
FIG. 2 is a diagram showing an exemplary architecture for the brainwave entrainment manager aspect of the brainwave entrainment using virtual objects and environments as visual, stimulation transducers.

FIG. 2 is a diagram showing an exemplary architecture for the brainwave entrainment manager aspect of the brainwave entrainment using virtual objects and environments as visual stimulation transducers. In this embodiment, the brainwave entrainment manager 200 comprises an entrainment routine selector 201, an attention evaluator 202, an in-game object activator 203, and an external transducer activator 204. The entrainment routine selector 201 receives input VR application input, therapy regimen controller input, and biometric sensor input, and input from the attention evaluator 202. Based on those inputs, the entrainment routine selector chooses and/or modifies a brainwave routine appropriate for the circumstances. For example, if the therapy regimen controller input specifies that the overall brainwave entrainment goal is relaxation, the entrainment routine selector 201 may select alpha wave entrainment as the primary entrainment therapy, and may choose to apply alpha wave entrainment to a background virtual object, as flashing of background objects will be less intrusive (and possibly more relaxing) to the user than flashing of objects to which the user's attention is directed. To determine which objects are not the subject of the user's attention, the attention evaluator 202 receives input from a spatial sensor (e.g., a camera used to track eye movements) to determine where the user is looking on the screen at a given moment. The entrainment routine selector 201 then modifies the entrainment routine to flash an object or objects at which the user is not looking using an in-game object activator 203 which interfaces with the VR application to identify which objects should be flashed.

The user's attention need not be tracked via a camera, and may be tracked through other means. For example, the user's attention may be tracked by monitoring the user's interaction with the virtual objects or virtual environment in the form of mouse clicks, keyboard activity, orientation of the user's head or body (e.g., when a virtual reality headset is being used), orientation and/or movement of hand-held trackable devices such as game controllers with integrated accelerometers, gyroscopes, etc. In some embodiments, the user's attention may be tracked not in terms of visual direction or attention, but in the more general sense of focus, consistency, ability to concentrate, level of interest, response times, or other factors not necessarily associated with the direction of the user's vision. All of these things may be incorporated into decisions by the entrainment routine selector 201 as to changes to be made to the entrainment routine.

Simultaneously, the entrainment routine selector 201 may activate one or more external transducers 204 using an external transducer activator 204, where the entrainment routine selector 201 determines that external transducers may supplement or complement the brainwave entrainment using virtual objects. The entrainment routine selector 201 may further use feedback to determine whether the selected entrainment routine is having the desired effect. As an example, the entrainment routine selector 201 may use biometric feedback such as a user's heart rate (e.g., a lowering heart rate may be used to infer relaxation) to change the entrainment routine. For example, a lowering heart rate during alpha wave entrainment would likely indicate relaxation, in which case the entrainment routine would remain unmodified, but a rising heart rate would likely indicate irritation, in which case the entrainment routine might be modified by reducing the entrainment to theta wave entrainment to further induce relaxation.

Many other types and implementations of feedback are possible including, but not limited to, changing of entrainment routines based on user reactions to, or interactions with, virtual objects and virtual environments; user attention attributes such as the location, intensity, focus, and consistency of user attention to virtual objects and virtual environments; game scores and other gaming metrics; physical biofeedback such as monitoring heart rate, perspiration, respiration; cognitive biofeedback such as monitoring changes in an EEG; exercise equipment feedback such as treadmill speed, cycling cadence and/or power, rowing strokes per minute and/or power. Further, entrainment routines can be changed to use different types of stimulation (e.g., if the feedback indicates that visual stimulation is less effective at certain points in a game, it can be supplemented with auditory or haptic feedback). Multiple stimulation devices can be used to augment or supplement the visual stimulation including, but not limited to, haptic headbands or vest, speakers or headphones, and other stimulation devices. In this way, the system can be programmed to automatically adapt to users based on a variety of feedback sources.

Detailed Description of Exemplary Aspects

Figure 3:
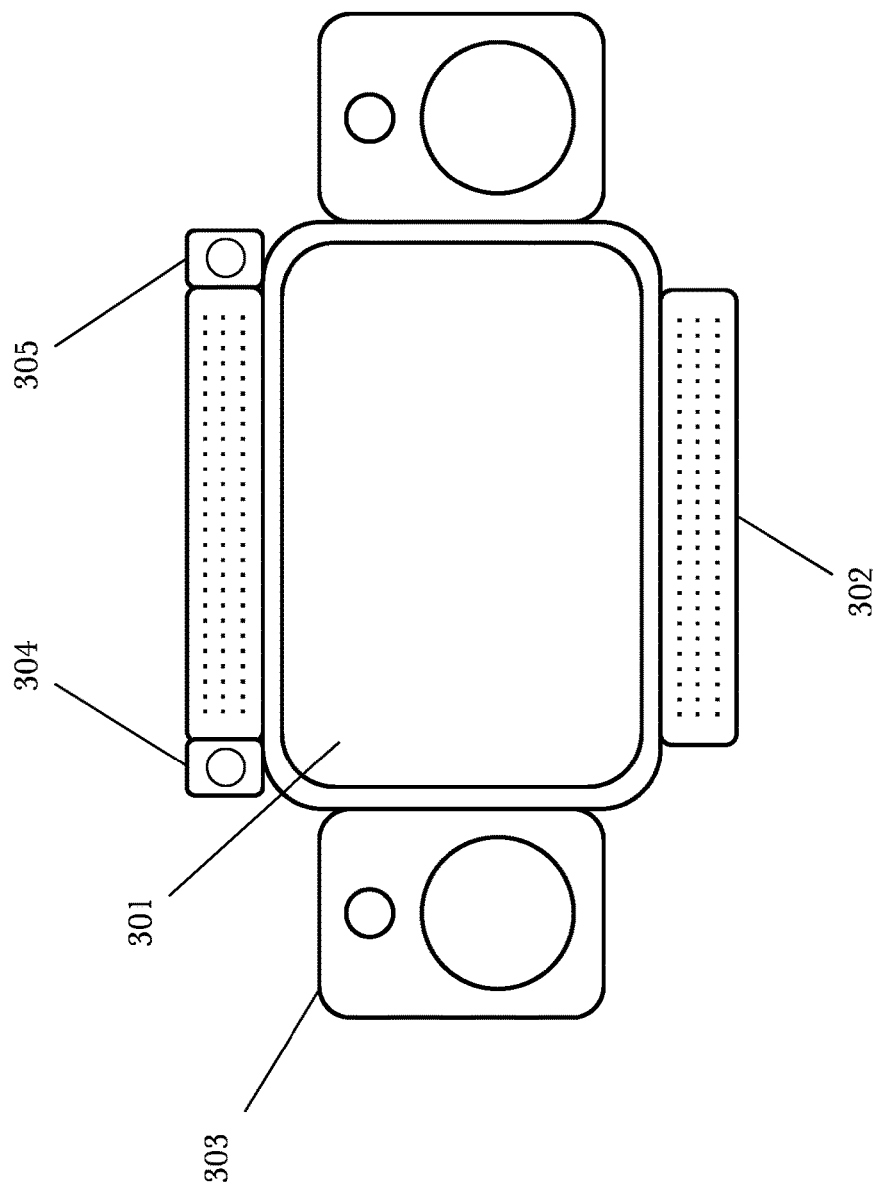
FIG. 3 is a diagram of an exemplary brainwave entrainment therapy device that can be attached to an exercise machine for targeted brainwave entrainment therapy with attention tracking and virtual objects.

FIG. 3 is a diagram of an exemplary brainwave entrainment therapy device that can be attached to an exercise machine for brainwave entrainment therapy with light and/or sound, including brainwave entrainment using virtual objects. In this embodiment, the brainwave entrainment device comprises a display 301, one or more lights 302, and one or more speakers or headphones 303. The display 301 is used for display of activities designed to engage the user in games or other activities while brainwave entrainment is applied using virtual objects on the display. The lights 302, shown here as light bars comprising multiple light-emitting diodes (LEDs) can be programmed to emit a supplemental visible stimulus (e.g., flashes, on/off cycles, etc.) at frequencies appropriate for brainwave entrainment. The speakers 303 can be programmed to emit a supplemental audible stimulus (e.g., rectangular wave sound pulses, sine wave sound oscillations, etc.) at frequencies appropriate for brainwave entrainment. In some configurations, both light and sound may be used as stimuli, separately or in conjunction with brainwave entrainment using virtual objects on the display 301. The stimuli need not be from the same source (e.g., two light sources each at 20 Hz could be synchronized to produce a 40 Hz stimulus) or from the same modality (e.g., a sound source at 15 Hz and a light source at 15 Hz could be synchronized to produce a 30 Hz stimulus)

The device of this embodiment is designed such that is can be mounted on an exercise machine (that may or may not be otherwise equipped for brainwave entrainment purposes), whereby it can be used to provide brainwave entrainment using virtual objects on the display 301, optionally with supplemental brainwave entrainment from the lights 302 and/or speakers 303. The use of virtual objects with brainwave entrainment allows for flexibility in applying brainwave entrainment. Brainwave entrainment using virtual objects provides essentially unlimited variability in terms of stimulator sizes, shapes, colors, movements, and allows for the use of multiple stimulators simultaneously, each with different characteristics. Further, gamification changes the brainwave stimulation from passive receipt of light therapy to active engagement with the visual stimulation objects, wherein the user's brain is actively stimulated during the activity, enhancing the effectiveness of the stimulation. Further, as the user is actively engaged with the virtual objects, stimulation can be applied based on where the user's attention is focused. Attention-based stimulation provides opportunities for both direct stimulation (e.g., flashing an object at which the user is looking) and indirect stimulation (e.g., flashing an object in the user's periphery of vision). For example, eye tracking technology can be used to determine where the user is looking on the screen at any given time, and objects at which the user is looking can be used to provide visual stimulation even if the user changes his or her attention to a different object on the screen. In this embodiment, an infrared emitter 304 emits an infrared light, which is reflected off the user's eye and cornea, and is received at an infrared-sensitive camera 305. The center of the eye is tracked in relation to a reflection from the cornea (the outer surface of the eye). The distance and direction of the difference between the center of the eye and the corneal reflection can be used to calculate the eye's position. Combined with a known distance to and size of the display 301 the location at which the user is looking can be determined. The user's attention to objects on the screen can be monitored over time to determine whether the user is remaining focused on the activity, or is getting tired and losing focus, and the determined level of user attention can be used to change the type, intensity, directness, and other characteristics of the stimulation.

Brainwave entrainment using virtual objects may be further enhanced by using multiple objects, each capable of providing complementary types of stimulation, and/or by intentionally directing the user's attention to objects providing certain types of stimulation. For example, if the user is playing a first person shooter (FPS) game that involves shooting attacking aliens, the user's attention will naturally be focused on finding attacking aliens, aiming at them, and shooting them. As each alien will be the focus of the user's attention sequentially, the alien at which the user is currently looking may be flashed at appropriate frequencies and in appropriate colors to provide appropriate brainwave stimulation. Simultaneously, other objects on the screen (or even the background) may be selected to provide a complementary visual stimulation in the periphery of the user's vision. Further, brainwave entrainment using virtual objects may be enhanced by selecting multiple treatment modalities (e.g., light, sound, vibration, electrical stimulation) applied either simultaneously or sequentially, by varying the frequency or frequencies of brainwave entrainment (e.g., from about 0.5 Hz to about 100 Hz), and by varying the intensity and/or scale of the treatment (e.g., from subtle, localized vibrational or electrical stimulation to area-wide, intense stimulation such as high-intensity room lighting and sound).

Application of brainwave entrainment using virtual objects and gamification allows for brainwave entrainment to target certain neurological functions by enhancing and concentrating the effect of the brainwave entrainment on the stimulated areas of the brain. As one example, a person with memory loss may be asked to play a memory-based card matching or tile matching game (mental activities which stimulate certain portions of the brain). While the person is engaged in the mental activity, brainwave entrainment is applied via the game objects on the display 301 and/or the lights 302 and/or speakers 303. As the neurological functions in the brain associated with memory are being stimulated, the neurons in the brain associated with those functions are in an already-stimulated state, and the brainwave entrainment's stimulation of oscillations in the electrochemical state of neurons in those already-stimulated areas will have a more pronounced effect than on other areas of the brain. In this way, the already-stimulated areas of the brain may experience a greater reduction in degenerative conditions (i.e., reductions in amyloid plaques and tau phosphorylation) and greater increases in synaptic density.

Figure 4:
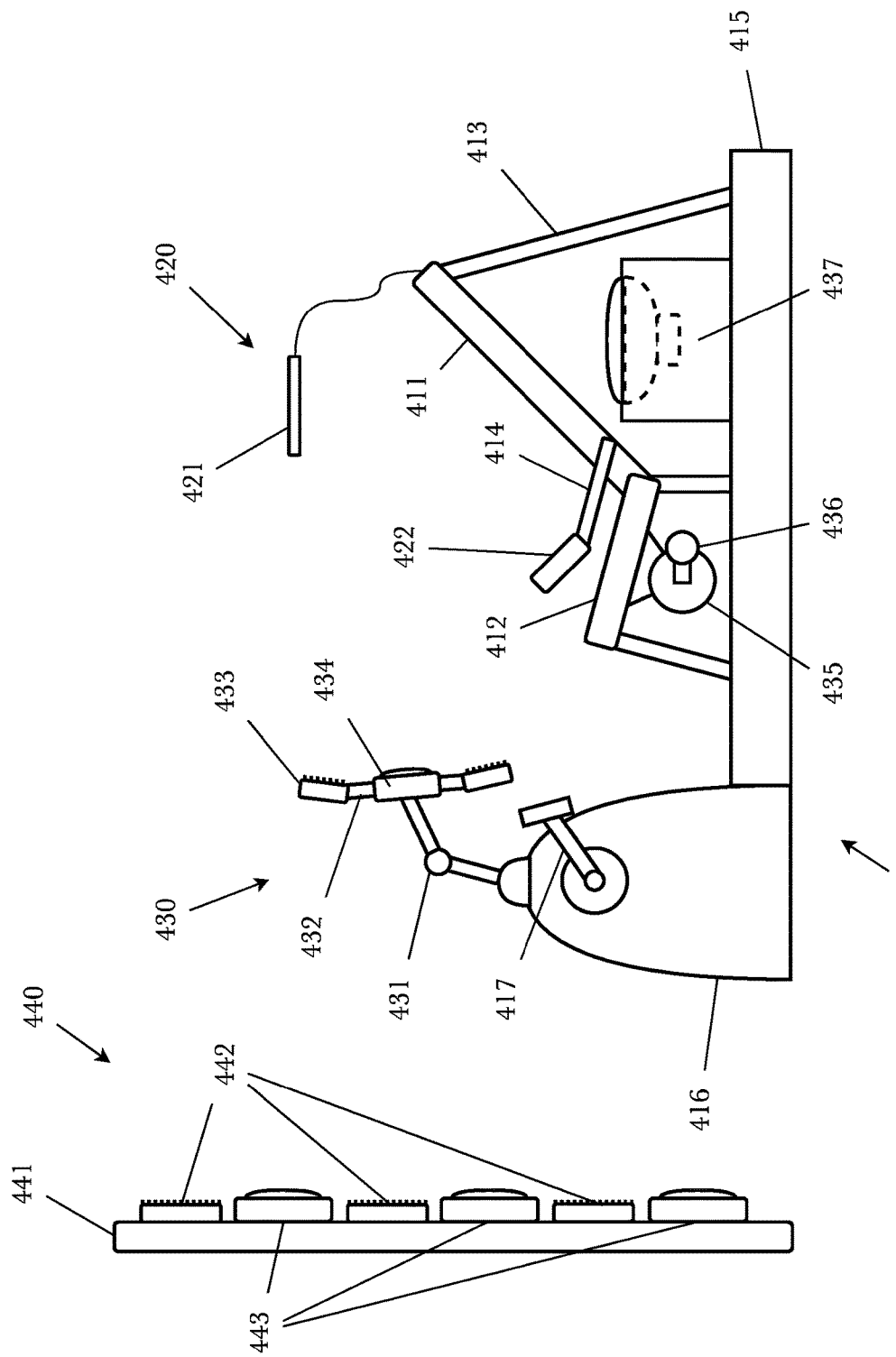
FIG. 4 is a diagram of an exemplary brainwave entrainment therapy system for brainwave entrainment therapy with attention tracking and virtual objects plus external stimulation transducers that allows for multi-modal, multi-intensity treatment.

FIG. 4 is a diagram of an exemplary brainwave entrainment therapy system for brainwave entrainment therapy that allows for multi-modal, multi-intensity therapies. The system 400 of this embodiment comprises a stationary recumbent bicycle 410, and three different scales of brainwave entrainment stimulators: localized and/or individual stimulation transducers 420, small area stimulation transducers 430, and large area stimulation transducers 440.

The stationary recumbent bicycle 410 comprises a base 415, a chair back 411, a seat 412, arm rests 414, a plurality of supports 413 connecting the chair back 411 and seat 412 to the base 415, a resistance mechanism 416 allowing for resistance to a pedaling motion of the user, and a pedal system 417 for the user to pedal in a cycling motion. The stationary recumbent bicycle 410 thus provides the means for the user to engage in a physical task in the case where dual task stimulation (and/or dual task assessment) is being applied.

The localized and/or individual stimulation transducers 420 of this embodiment are a headband 421 with vibratory stimulation and hand grips 422 which provide electrical stimulation. These provide localized stimulation which can only be perceived by the user, which also makes them individual stimulation transducers (as opposed to the other scales, which can be perceived by others, and which could be used to provide brainwave entrainment to more than one person using the same transducer(s)). The headband 421 may produce simple vibratory (i.e., tactile) stimulation to the head, or may be configured to produce vibrations at certain locations on the head and at certain intensities so as to be perceptible by the middle and inner ear, which causes the stimulation to be both tactile and auditory in nature. This double stimulation (tactile and auditory) amplifies the effect of a single type of transducer, increasing the efficiency of brainwave entrainment from applications of that transducer.

The small area stimulation transducers 430 of this embodiment are devices attached to the exercise machine 410, but not directly attached to or in contact with the user. For example, a console comprising a display 432, light bars 433, and speakers 434 similar to that of the device of FIG. 33 may be used. The console may be attached to the exercise machine using an adjustable arm 431 that allows for optimal positioning of the console for viewing and/or interaction by the user. Other small area stimulation transducers include a large electric motor 435 with an offset weight 436 attached to the seat 412 that allows for full-body vibratory stimulation to be applied, and a subwoofer 437 under the chair back 411 that allows for both audible (regular sound) and inaudible (infrasound) stimulation to be applied. Small area stimulation transducers are particularly useful in situations where direct contact with a user is not desirable, or when multiple users will be using the device sequentially, or when brainwave entrainment will be applied to a small number of users (e.g., those directly in front of the stimulation transducers). The display 432 may be used to provide brainwave entrainment using virtual objects in conjunction with gamification.

The large area stimulation transducers 440 of this embodiment are devices that can be used over a large area and potentially a large number of persons such as a room or auditorium. In this embodiment, The large area stimulation transducers are large LED light bars 442 and large speakers 443 attached to a wall 441 of the room in which the stimulation will be applied. The large area stimulators such as the LED light bars 442 and large speakers 443 on the wall 441 can be used to fully immerse the user in intense brainwave entrainment with large areas of bright light and loud, booming sounds. The immersion and intensity can be enhanced, for example, by surrounding the user with large area stimulators on walls on all sides (and possibly ceilings and floors) covering the user's entire visual area, so that the user receives visual stimulation no matter in which direction the user looks an auditory stimulation no matter where the user is located. Higher immersion and intensity may provide greater beneficial effects from brainwave entrainment.

It is important to note that any type of transducer can be applied at any scale. For example, light stimulation can be configured such that it is seen only by one person (e.g., in glasses or goggles), or is seen by a small number of persons (e.g., a single LED light bar), or is seen by many people (e.g. room lights, stadium lights, etc.). Further, the intensity of stimulation can be largely varied separately from the scale of stimulation. However, depending on the circumstances and application, brainwave entrainment at certain scales and/or intensities may be more useful or effective than at others.

The different scales of stimulation transducers allow for a choice of the level of immersion the user experiences with respect to the brainwave entrainment, and to some degree, the level of intensity of the brainwave entrainment. Immersion is the quality of being surrounded by or absorbed in an experience. Intensity is the magnitude of the experience. They are separate qualities (e.g., a localized electric stimulation can be intense, but not immersive), but there can be an increase in intensity with an increase in scale (for example, if light stimulation comes from all directions, it will tend to be both more immersive and more intense, although the intensity of the lights can be reduced to offset this tendency). For example, a localized, subtle electrical stimulation through electrically-conducting hand grips 422 provides minimal immersion of the user in the brainwave entrainment. This may be useful, for example, where intense concentration on the dual task stimulation is necessary. Small area stimulation transducers such as the LED light bars 433 on the screen console are useful for mid-level immersion and mid-level intensity of brainwave entrainment. The LED light bars 433 cover a small, but significant, area of the user's view, and the speakers 44 are large enough to provide a substantial auditory stimulus. The large area stimulators such as the LED light bars 442 and large speakers 443 on the wall 441 can be used to fully immerse the user in intense brainwave entrainment with large areas of bright light and loud, booming sounds. The immersion and intensity can be enhanced, for example, by surrounding the user with large area stimulators on walls on all sides (and possibly ceilings and floors) covering the user's entire visual area, so that the user receives visual stimulation no matter in which direction the user looks an auditory stimulation no matter where the user is located. Higher immersion and intensity may provide greater beneficial effects from brainwave entrainment.

Further, it is important to note that the modalities (types of stimulation), scales, and intensities allows for tremendous flexibility in selecting suitable therapies regimens for different situations. For high-immersion scenarios (e.g., maximum brainwave entrainment with fewer cognitive demands such as listening to music), multiple modalities, scales, and intensities may be used at the same time. For example, while a user is listening to classical music, localized electrical stimulation may be applied to the wrist, small area visual stimulation may be applied using a single LED light bar, and large area tactile stimulation may be applied using subwoofers which produce sounds (infrasounds) which are inaudible to the human ear but can be perceived through the sense of touch (e.g., as oscillating pressure on the torso).

Further, modalities can be chosen to either amplify certain tasks or activities or to supplement them. For amplification, treatment modalities are chosen to include those corresponding to a given task or activity in gamification. As an example, if a user is assigned a game activity wherein the user must follow a moving object on the display with his or her eyes, the object can be flashed at 40 Hz for gamma entrainment therapy. As the user is already focused on the object, the user is focusing more intensely on visual activities (and the brain areas and functions associated with visual activities are stimulated), enhancing the effect of the visual gamma entrainment modality. For supplementation, treatment modalities are chosen to exclude those corresponding to a gamification task. As an example, if game activity assigned to a user is identifying songbirds presented on the display, flashing the birds at 40 Hz (or otherwise changing their colors or visual appearance) may interfere with the identification process. In such circumstances, a non-conflicting modality may be chosen such as flashing of background objects or supplementation with audible entrainment.

Figure 5A:
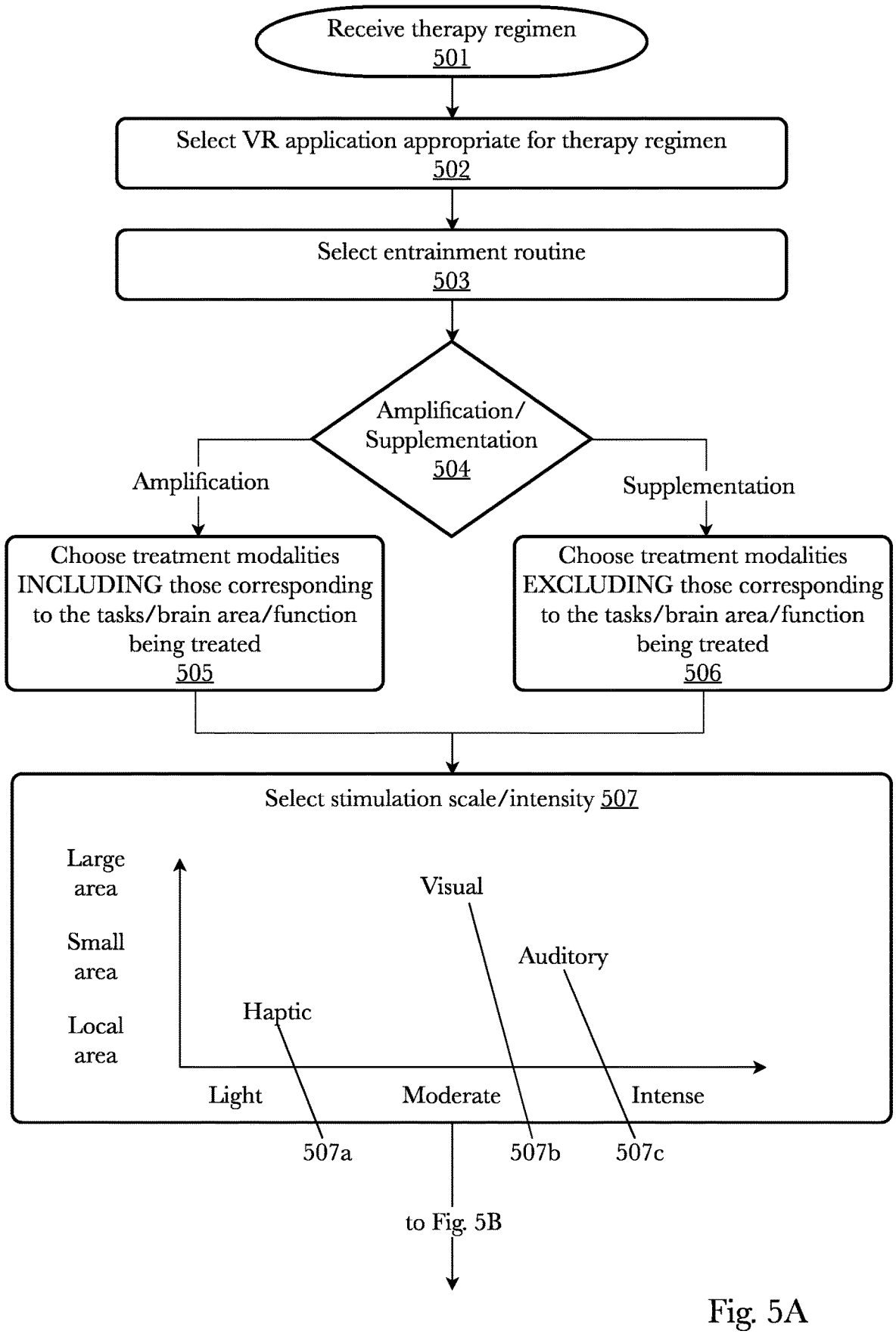
FIGS. 5A & 5B are a flow diagrams showing an algorithm for selection of modalities and routines for brainwave entrainment and application of brainwave entrainment using a virtual environment using eye tracking and biometric feedback to select virtual objects and entrainment routines.
Figure 5B:
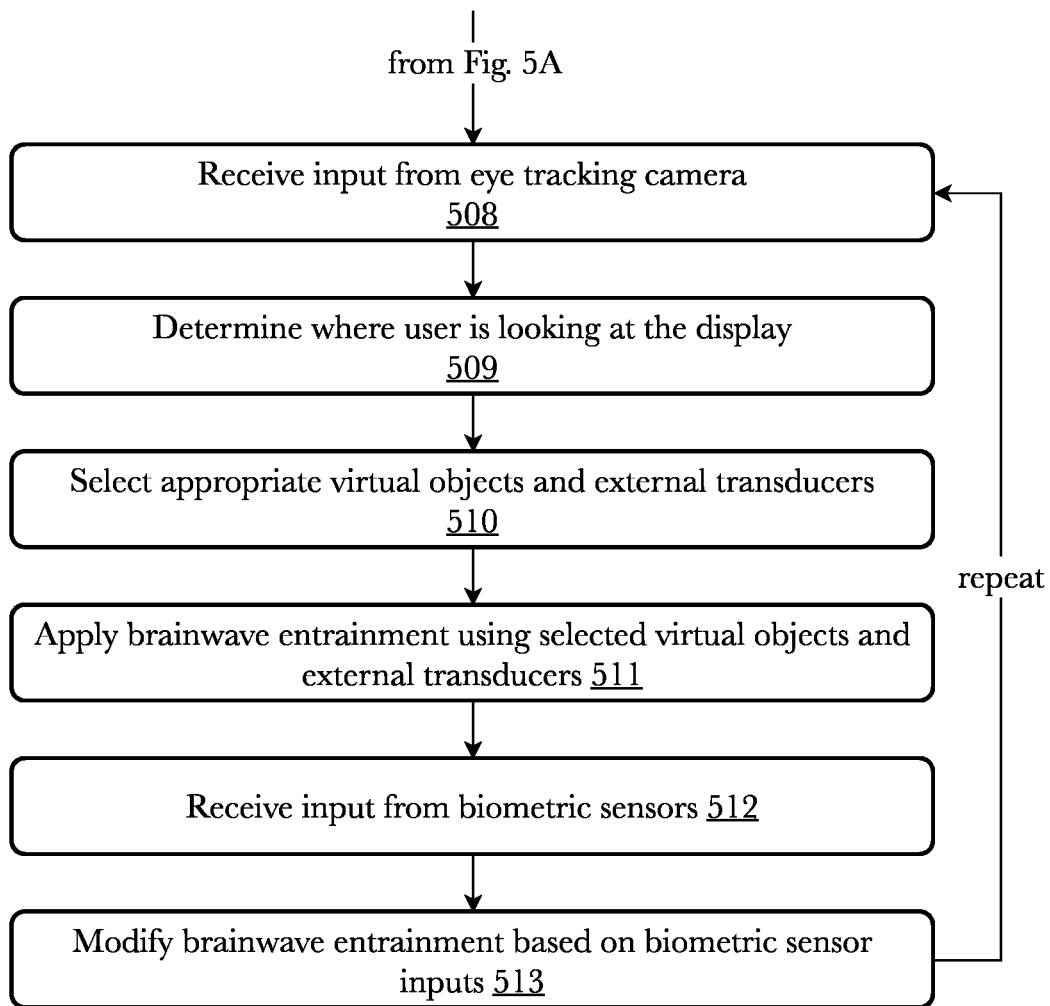

FIGS. 5A & 5B are a flow diagram showing an algorithm for selection of modalities and routines for brainwave entrainment and application of brainwave entrainment using a virtual environment using eye tracking and biometric feedback to select virtual objects and entrainment routines. As a first step, a therapy regimen is received 501 The therapy regimen may be received from any source providing instructions for brainwave entrainment, such as a database, an administrator (e.g., a physician, therapist, masseuse, or other service provider) for application to a user (who may be a patient, client, etc., of the administrator), or from the user himself or herself. An example therapy regimen would be a regimen for brainwave entrainment that emphasizes alpha wave stimulation to induce relaxation in an overstimulated user.

A suitable VR application or other gamification application is then chosen 502, which ideally should be consistent in content with the nature of the therapy regimen chosen. For example, if the therapy regimen is a regimen for brainwave entrainment that emphasizes alpha wave stimulation to induce relaxation in an overstimulated user, a VR application might be chosen that involves causal cycling along a forest path. If a more stimulating therapy regimen is chosen, for example something involving intense concentration and gamma wave therapy, a first person shooter might be chosen.

Based on the therapy regimen and VR application chosen, an entrainment routine is selected 503. For example, if the therapy regimen specifies that the overall brainwave entrainment goal is relaxation, the entrainment routine selected 503 may use alpha wave entrainment as the primary entrainment therapy, and may choose to apply alpha wave entrainment to a background virtual object (e.g., the sky or trees in the background of the casual cycling along the forest path), as flashing of background objects will be less intrusive (and possibly more relaxing) to the user than flashing of objects to which the user's attention is directed (e.g., the path or direction of the virtual bicycle). Selection of the entrainment routine 503 may further involve selecting amplification or supplementation 504 as appropriate for the circumstances, choosing appropriate treatment modalities (e.g., light therapy, sound therapy, vibrational therapy, electrical therapy, or combinations of such modalities) either for amplification 505 (treatments including those corresponding to the tasks, activities, or neurological function) or for supplementation 506 (treatments including those corresponding to the tasks, activities, or neurological function), and selecting a stimulation scale and intensity 507 for each modality appropriate for the treatment goals. In this example, three modalities are shown with different scales and intensities, localized haptic stimulation at a light intensity 507a, large area visual stimulation at a moderate intensity 507b, and small area auditory stimulation at a moderately intense intensity 507c. Brainwave entrainment is then applied using the chosen regimen, providing targeted treatment of particular areas of the brain and/or particular neurological functions via stimulation of those areas or functions using dual task stimulation.

At this point, a camera may be used to track the user's eye movements 508 to determine where the user is looking on the screen at a given moment 509. Based on the above inputs, appropriate virtual objects are chosen to apply brainwave entrainment by modifying virtual objects on the screen 510, which modification may take any number of forms (e.g., objects may be flashed at specific frequencies, the color of objects may be changed at specific frequencies, the size of objects may be changed at specific frequencies, objects may be rotated at specific frequencies, etc.). Any change to a virtual object that is perceptible to a user and can be applied at a repeating frequency (i.e., oscillating frequency) may be used to apply brainwave entrainment. Brainwave entrainment is applied using the virtual objects, optionally supplemented with entrainment from external transducers 511.

Input from biometric feedback (e.g., the user's heart rate) is received 512 and evaluated to determine whether the selected entrainment routine is having the desired effect (e.g., a lowering heart rate may be used to infer relaxation), and to change the entrainment routine, accordingly 513. For example, a lowering heart rate during alpha wave entrainment would likely indicate relaxation, in which case the entrainment routine would remain unmodified, but a rising heart rate would likely indicate irritation, in which case the entrainment routine might be modified by reducing the entrainment to theta wave entrainment to further induce relaxation. The process of tracking the user's attention and applying appropriate modifications to brainwave entrainment is repeated from step 508 until the therapy session ends.

Figure 6:
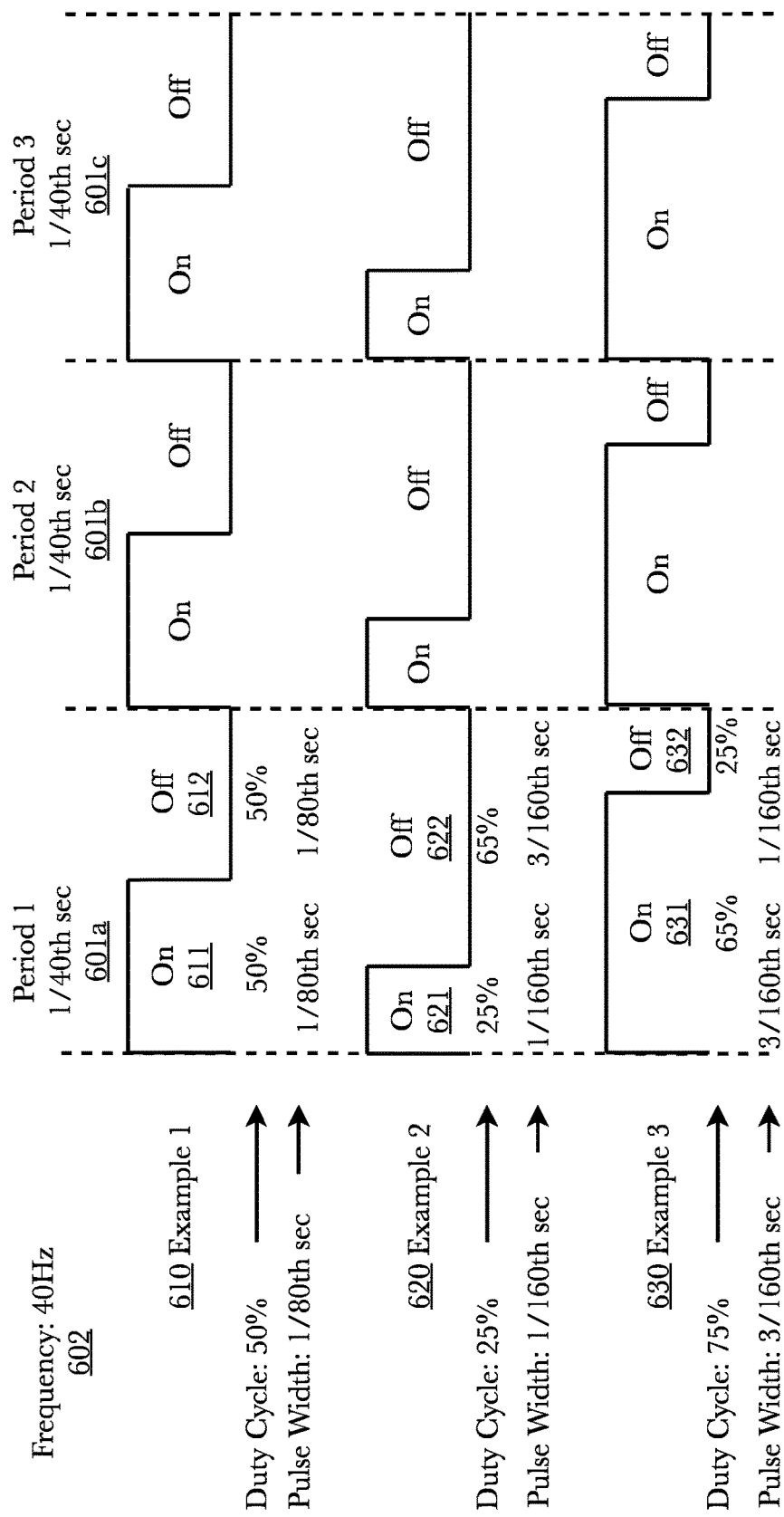
FIG. 6 is a diagram explaining the use of duty cycles and pulse width modulations in applying brainwave entrainment.

FIG. 6 is a diagram showing explaining the use of duty cycles and pulse width modulations in applying brainwave entrainment. Here, three examples 610, 620, and 630 of duty cycles/pulse width modulation are shown. The frequency of stimulation 602 in all three examples is 40 Hz (40 cycles per second), and the wave form of each example is a rectangular wave (i.e., instantaneous or near-instantaneous changes between on and off states). Three periods 601a-c of the stimulation at the 40 Hz frequency 602 are shown, each period corresponding to one full on/off cycle lasting $1/40^{th}$ of one second. In Example 1 610, a duty cycle of 50% is shown in which the stimulation is in an on state 611 for 50% of the period and in an off state 612 for 50% of the period. For a 40 Hz frequency as shown here, this corresponds to a pulse width of $1/80^{th}$ of a second, wherein the stimulation is in an on state 611 for $1/80^{th}$ of a second and in an off state 612 for $1/80^{th}$ of a second. In Example 2 620, a duty cycle of 25% is shown in which the stimulation is in an on state 621 for 25% of the period and in an off state 622 for 75% of the period. For a 40 Hz frequency as shown here, this corresponds to a pulse width of $1/160^{th}$ of a second, wherein the stimulation is in an on state 621 for $1/160^{th}$ of a second and in an off state 622 for $3/160^{th}$ of a second. In Example 3 630, a duty cycle of 75% is shown in which the stimulation is in an on state 631 for 75% of the period and in an off state 632 for 25% of the period. For a 40 Hz frequency as shown here, this corresponds to a pulse width of $3/160^{th}$ of a second, wherein the stimulation is in an on state 631 for $3/160^{th}$ of a second and in an off state 632 for $1/160^{th}$ of a second.

FIGS. 7-9 explain the application of eye tracking technology as a means of determining where a user is looking. In one form of eye tracking technology, an infrared emitter 720 emits an infrared light 721, which is reflected off the user's eye 701 and cornea, and is received 731 at an infrared-sensitive camera 730. The image of the of the user's eye appears to the camera substantially as shown in FIG. 9, wherein the sclera (the white part of the eye) 901, the iris (the colored part of the eye) 902, and the pupil (the opening in the eye) 903 are visible. The center of the eye 910 is tracked, as shown by a first set of crosshairs 911, in relation to a reflection from the cornea (the outer surface of the eye) 920, as shown by a second set of crosshairs 921. The distance and direction of the difference between the center of the eye and the corneal reflection can be used to calculate the eye's position. Combined with a known distance to and size of a display, 740, the location at which the user is looking 702 can be determined. FIG. 8 shows the same application of eye tracking technology, but inside a VR headset 840. In FIG. 8, an infrared emitter 820 emits an infrared light 821, which is reflected off the user's eye 801 and cornea, and is received 832 at an infrared-sensitive camera 830. The distance and direction of the difference between the center of the eye and the corneal reflection can be used to calculate the eye's position. Combined with a known distance to and size of a display, 841, the location at which the user is looking 802 can be determined.

FIG. 10 is a diagram showing an embodiment in which on-screen virtual objects on a display are used to apply brainwave entrainment. In this example, brainwave entrainment is implemented using a display 1010, such as a television computer monitor, or tablet-based device, comprising a screen 1011 and in some configurations, built in speakers 1031a,b. In this embodiment, the screen 1011 is used to provide visual brainwave entrainment, either by flashing the background of the screen 1011 or one or more on-screen virtual objects 1020. This embodiment enables the provision of brainwave entrainment without the use of (or in addition to) external devices such as lights and speakers. In this example, five on-screen virtual objects 1020 are shown 1021-1025, each comprising a different shape and each moving independently on the screen 1011 as indicated by the dashed and dotted "movement shadows" associated with each on-screen virtual objects 1020. The on-screen virtual objects 1020 are generic shapes in this diagram, but may represent any type of on-screen element whether static or movable, permanent or transient. Depending on the configuration, the on-screen element may be any shape or color displayable on a screen, such as game elements, puzzle elements, background elements, regular or irregular portions of the screen. Many possible applications of this embodiment are possible. The built-in speakers, if any, may be used to provide auditory brainwave entrainment in addition to the visual on-screen brainwave entrainment.

For example, when paired with a camera and eye-tracking software, the on-screen virtual objects 1020 might represent an eye muscle strengthening exercise combined with brainwave entrainment, wherein the user is asked to find a target on-screen virtual object with a particular shape and follow the shape with his or her eyes. At the same time the target virtual object may flash a particular color at a selected brainwave entrainment frequency, with the color changing as the user's eyes either follow the target on-screen virtual object or stray from it. The target on-screen virtual object may, for example, be a pleasant light-blue color while the user's eyes are following it, and change to a bright red to re-attract the user if the user's eyes start following a different on-screen element.

In this embodiment, a clip-on eye-tracking unit 1040 may be attached to the display 1010 using plastic (or other material) clips 1044. The clip-on eye-tracking unit 1040 comprises a housing 1041, an infrared emitter 1042 which emits an infrared light that is reflected off the user's eye and cornea, and is received at an infrared-sensitive camera 1043, and clips 1044 which may be used to attach the clip-on eye-tracking unit 1040 to a display 1010. The center of the eye is tracked in relation to a reflection from the cornea (the outer surface of the eye). The distance and direction of the difference between the center of the eye and the corneal reflection can be used to calculate the eye's position. Combined with a known distance to and size of the display 1010 the location at which the user is looking can be determined.

In another use case, the on-screen virtual objects 1020 may represent a puzzle or game, and the brainwave entrainment may be provided by simply flashing the screen background 1012 at a selected brainwave entrainment frequency.

This example may be extended to virtual reality applications, wherein brainwave entrainment is provided by flashing in-game elements within the virtual reality environment.

FIG. 11 is a diagram showing an exemplary virtual reality environment in which virtual objects may be used as visual stimulation transducers. The virtual reality environment show in this diagram depicts a quiet scene from a first person perspective, and would be suitable for brainwave entrainment related to theta or alpha wave entrainment (for example, to facilitate relaxation, creativity, exploration, and contemplation). The environment comprises a room with a floor 1110, a ceiling 1112, and three visible walls 1111a-c. In the ceiling are four recessed lights 1113. On the left wall 1111a is a flat-screen television 1123 showing an outdoor scene 1124 involving mountains, trees, and lightning. On the right wall 1111c is a door 1114. On the back wall is a window to the outside 1115 in which the sun can be seen 1130. In the corner of the room is a potted plant 1122, and next to the back wall 1111*b* is a table 1120 on which is standing a lamp 1121. Each and every virtual object named above can be used to provide brainwave entrainment. For example, any one or all of the virtual lighting objects, the lamp 1121, the television, 1124, the ceiling lights 1113, and the sun 1130 could be flashed or changed in intensity at the selected brainwave entrainment frequency. Even objects not associated with lighting, such as the walls 1111*a-c*, ceiling 1112, floor 1110, or door 1114, could be flashed or changed. If appropriate to the therapy regimen selected, exploration and curiosity could be encouraged by flashing certain objects (e.g., the television 1124, the potted plant 1122, the table 1120, the door 1114) as the user investigates or interacts with them. With some additions, a scene such as the one depicted here could be used to perform brainwave entrainment in a mystery or other storyline. Other modalities of brainwave entrainment such as sound and haptic feedback may be applied simultaneously with the visual stimulation. As more fully described above, these other modalities may be applied using either the same or different brainwave entrainment frequencies. As a non-limiting example, if a user in the virtual reality environment switches on the lamp 1121, not only might the lamp 1121 flash or change color at a brainwave entrainment frequency as a form of visual stimulation, an audible tone might be generated corresponding to the lamp flickering at the same entrainment frequency, and haptic feedback in the form of vibration of a game controller might also be applied. In some applications, for example in virtual environments comprising a darkened environment such as a room with the lights turned off, the visual stimulation may not be used, but the auditory and/or haptic stimulation modalities may continue to be applied.

FIG. 12 is a diagram showing exemplary gamification of brainwave entrainment in which in-game objects and elements are used as visual stimulation transducers in conjunction with gameplay activities. The gameplay example shown here depicts a first person shooter (FPS) involving shooting of attacking aliens, and would be suitable for brainwave entrainment related to beta or gamma wave entrainment (for example, to facilitate concentration, planning, or problem-solving). The environment comprises a laser gun 2120 controllable by the user, a spaceship 2112, a space background 2113 comprising stars 2110, and a plurality of attacking aliens 2111. The laser gun 2120 is shown here with a laser flash 2121, the resulting laser beam 2122, and its impact 2123 on one of the attacking aliens 2111. Each and every virtual object named above can be used to provide brainwave entrainment. For example, aliens 2111 may be flashed or changed as the user's attention focuses on them. The laser flash 2121, laser beam 2122, and impact 2123 can all be used to provide bright visual stimulation at an appropriate frequency during game play. Even the background 2113 and stars 2110 could be changed in color or brightness at an appropriate frequency.

In some embodiments, virtual reality environments and games could be used to provide entrainment opposite of the common expectation. For example, in the calm room shown in FIG. 11, gamma wave brainwave entrainment associated with concentration and planning could be applied to increase the user's awareness when in calm or innocuous-looking environments. Similarly, while playing an intense FPS such as that shown in FIG. 12, theta or alpha wave entrainment could be applied to calm the user during otherwise-intense game play. In a related use case where a user is addicted to the adrenalin received from intense game play, theta or alpha brainwave entrainment could be used to reduce the player's addition to games by calming the player during intense game play, reducing the adrenalin rush from playing highly-immersive, fast-action games with intense themes.

Other modalities of brainwave entrainment such as sound and haptic feedback may be applied simultaneously with the visual stimulation. As more fully described above, these other modalities may be applied using either the same or different brainwave entrainment frequencies. As a non-limiting example, when the user in the virtual reality environment shoots the alien 2111, not only might the impact 2123 provide visual brainwave entrainment, but an audible tone might be generated corresponding to the flashing or color changing of the impact 2123 at the same entrainment frequency, and haptic feedback in the form of vibration of a game controller might also be applied. In some applications, for example in virtual environments comprising a darkened environment, the visual stimulation may not be used, but the auditory and/or haptic stimulation modalities may continue to be applied.

Hardware Architecture

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the embodiments disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific embodiments, at least some of the features or functionalities of the various embodiments disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some embodiments, at least some of the features or functionalities of the various embodiments disclosed herein may be implemented in one or more virtualized computing environments (e.g., network computing clouds, virtual machines hosted on one or more physical computing machines, or other appropriate virtual environments).

Referring now to FIG. 13, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network a metropolitan area network, a local area network, a wireless network, the Internet, or any other network, using known protocols for such communication, whether wireless or wired.

In one embodiment, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one embodiment, a computing device 10 may be configured or designed to function as a server system utilizing CPU 12, local memory 11 and/or remote memory 16, and interface(s) 15. In at least one embodiment, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some embodiments, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a specific embodiment, a local memory 11 (such as non-volatile random access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one embodiment, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 13 illustrates one specific architecture for a computing device 10 for implementing one or more of the inventions described herein, it is by no means the only device architecture on which at least a portion of the features and techniques described herein may be implemented. For example, architectures having one or any number of processors 13 may be used, and such processors 13 may be present in a single device or distributed among any number of devices. In one embodiment, a single processor 13 handles communications as well as routing computations, while in other embodiments a separate dedicated communications processor may be provided. In various embodiments, different types of features or functionalities may be implemented in a system according to the invention that includes a client device (such as a tablet device or smartphone running client software) and server systems (such as a server system described in more detail below).

Regardless of network device configuration, the system of the present invention may employ one or more memories or memory modules (such as, for example, remote memory block 16 and local memory 11) configured to store data, program instructions for the general-purpose network operations, or other information relating to the functionality of the embodiments described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

Because such information and program instructions may be employed to implement one or more systems or methods described herein, at least some network device embodiments may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

In some embodiments, systems according to the present invention may be implemented on a standalone computing system. Referring now to FIG. 14, there is shown a block diagram depicting a typical exemplary architecture of one or more embodiments or components thereof on a standalone computing system. Computing device 20 includes processors 21 that may run software that carry out one or more functions or applications of embodiments of the invention, such as for example a client application 24. Processors 21 may carry out computing instructions under control of an operating system 22 such as, for example, a version of MICROSOFT WINDOWS™ operating system, APPLE MACOS™ or iOS™ operating systems, some variety of the Linux operating system, ANDROID™ operating system, or the like. In many cases, one or more shared services 23 may be operable in system 20, and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 13). Examples of storage devices 26 include flash memory, magnetic hard drive, CD-ROM, and/or the like.

In some embodiments, systems of the present invention may be implemented on a distributed computing network, such as one having any number of clients and/or servers. Referring now to FIG. 15, there is shown a block diagram depicting an exemplary architecture 30 for implementing at least a portion of a system according to an embodiment of the invention on a distributed computing network. According to the embodiment, any number of clients 33 may be provided. Each client 33 may run software for implementing client-side portions of the present invention; clients may comprise a system 20 such as that illustrated in FIG. 14. In addition, any number of servers 32 may be provided for handling requests received from one or more clients 33. Clients 33 and servers 32 may communicate with one another via one or more electronic networks 31, which may be in various embodiments any of the Internet, a wide area network, a mobile telephony network (such as CDMA or GSM cellular networks), a wireless network (such as WiFi, WiMAX, LTE, and so forth), or a local area network (or indeed any network topology known in the art; the invention does not prefer any one network topology over any other). Networks 31 may be implemented using any known network protocols, including for example wired and/or wireless protocols.

In addition, in some embodiments, servers 32 may call external services 37 when needed to obtain additional information, or to refer to additional data concerning a particular call. Communications with external services 37 may take place, for example, via one or more networks 31. In various embodiments, external services 37 may comprise web-enabled services or functionality related to or installed on the hardware device itself. For example, in an embodiment where client applications 24 are implemented on a smartphone or other electronic device, client applications 24 may obtain information stored in a server system 32 in the cloud or on an external service 37 deployed on one or more of a particular enterprise's or user's premises.

In some embodiments of the invention, clients 33 or servers 32 (or both) may make use of one or more specialized services or appliances that may be deployed locally or remotely across one or more networks 31. For example, one or more databases 34 may be used or referred to by one or more embodiments of the invention. It should be understood by one having ordinary skill in the art that databases 34 may be arranged in a wide variety of architectures and using a wide variety of data access and manipulation means. For example, in various embodiments one or more databases 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some embodiments, variant database architectures such as column-oriented databases, in-memory databases, clustered databases, distributed databases, or even flat file data repositories may be used according to the invention. It will be appreciated by one having ordinary skill in the art that any combination of known or future database technologies may be used as appropriate, unless a specific database technology or a specific arrangement of components is specified for a particular embodiment herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, most embodiments of the invention may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with embodiments of the invention without limitation, unless a specific security 36 or configuration system 35 or approach is specifically required by the description of any specific embodiment.

FIG. 16 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to keyboard 49, pointing device 50, hard disk 52, and real-time clock 51. NIC 53 connects to network 54, which may be the Internet or a local network, which local network may or may not have connections to the Internet. Also shown as part of system 40 is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

In various embodiments, functionality for implementing systems or methods of the present invention may be distributed among any number of client and/or server components. For example, various software modules may be implemented for performing various functions in connection with the present invention, and such modules may be variously implemented to run on server and/or client components.

The skilled person will be aware of a range of possible modifications of the various embodiments described above. Accordingly, the present invention is defined by the claims and their equivalents.

What is claimed is:

1. A system for game-based brainwave entrainment, comprising:
    a computing device comprising a memory and a processor;
    a stimulation transducer; and
    a brainwave entrainment manager comprising a first plurality of programming instructions stored in the memory and operating on the processor, wherein the first plurality of programming instructions, when operating on the processor, causes the computing device to:
    receive a therapy regimen for brainwave entrainment;
    select an entrainment frequency or range of entrainment frequencies based on the therapy regimen;
    receive feedback from a game application comprising a determination of a user's level of attention toward the game application, wherein the determination is based on a monitored interaction of the user with the game application;
    change the selected entrainment frequency or range of entrainment frequencies based on the feedback; and
    based on the received therapy regimen, instruct the game application to change a state of the stimulation transducer at the selected entrainment frequency or range of entrainment frequencies;
    wherein the game application comprises a second plurality of programming instructions stored in the memory and operating on the processor, wherein the second plurality of programming instructions, when operating on the processor, causes the computing device to:
    provide one or more opportunities for user interaction within the game application;
    receive the instruction to change the state of the stimulation transducer; and
    change the state of the stimulation transducer at the selected entrainment frequency or range of entrainment frequencies.

2. The system of claim 1, further comprising a biometric sensor configured to measure biometric data pertaining to the user, and wherein the feedback comprises the biometric data.

3. The system of claim 2, wherein the biometric sensor is a heart rate monitor and the biometric data is a heart rate of a person.

4. The system of claim 2, wherein the biometric sensor is an electroencephalograph (EEG) and the biometric data is an electrical activity of the user's brain.

5. The system of claim 1, further comprising a spatial sensor configured to measure a location in physical space, and wherein the feedback comprises a measurement from the spatial sensor.

6. The system of claim 5, wherein the spatial sensor is an eye-tracking sensor.

7. The system of claim 1, further comprising a display, and wherein the stimulation transducer is a virtual object on the display.

8. The system of claim 1, wherein the stimulation transducer is selected from the list of a visual stimulation transducer, an auditory stimulation transducer, a vibratory stimulation transducer, a haptic headband comprising vibratory feedback, and a game controller comprising vibratory feedback.

9. A method for game-based brainwave entrainment, comprising the steps of:
    receiving, at a brainwave entrainment manager operating on a computing device, a therapy regimen for brainwave entrainment;
    selecting an entrainment frequency or range of entrainment frequencies based on the therapy regimen;
    receiving feedback from a game application comprising a determination of a user's level of attention toward the game application, wherein the determination is based on a monitored interaction of the user with the game application;
    changing the selected entrainment frequency or range of entrainment frequencies based on the feedback;
    providing one or more opportunities for user interaction within the game application;
    based on the received therapy regimen, instructing the game application to change a state of a stimulation transducer at the selected entrainment frequency or range of entrainment frequencies; and
    changing, using the game application, the state of the stimulation transducer at the selected entrainment frequency or range of entrainment frequencies.

10. The method of claim 9, further comprising the step of using a biometric sensor to measure biometric data from the user, and wherein the feedback comprises the biometric data.

11. The method of claim 10, wherein the biometric sensor is a heart rate monitor and the biometric data is a heart rate of a person.

12. The method of claim 10, wherein the biometric sensor is an electroencephalograph (EEG) and the biometric data is an electrical activity of a person's brain.

13. The method of claim 9, further comprising the step of using a spatial sensor to measure a location in physical space, and wherein the feedback comprises a measurement from the spatial sensor.

14. The method of claim 13, wherein the spatial sensor is an eye-tracking sensor.

15. The method of claim 9, further comprising the step of providing a display, and wherein the stimulation transducer is a virtual object on the display.

16. The method of claim 9, wherein the stimulation transducer is selected from the list of a visual stimulation transducer, an auditory stimulation transducer, a vibratory stimulation transducer, a haptic headband comprising vibratory feedback, and a game controller comprising vibratory feedback.

\* \* \* \* \*